US005693517A

United States Patent [19]
Gelfand et al.

[11] Patent Number: 5,693,517
[45] Date of Patent: Dec. 2, 1997

[54] REAGENTS AND METHODS FOR COUPLED HIGH TEMPERATURE REVERSE TRANSCRIPTION AND POLYMERASE CHAIN REACTIONS

[75] Inventors: David H. Gelfand, Oakland; Thomas W. Myers, Alameda; Christopher L. Sigua, Antioch, all of Calif.

[73] Assignee: Roche Molecular Systems, Inc., Branchburg, N.J.

[21] Appl. No.: 384,817

[22] Filed: Feb. 2, 1995

Related U.S. Application Data

[63] Continuation of Ser. No. 86,483, Jul. 1, 1993, abandoned, which is a continuation-in-part of Ser. No. 82,182, Jun. 24, 1993, Pat. No. 5,310,652, Ser. No. 880,478, May 6, 1992, abandoned, and Ser. No. 960,362, Jan. 5, 1993, Pat. No. 5,418,149, which is a continuation-in-part of Ser. No. 609,157, Nov. 2, 1990, abandoned, which is a continuation-in-part of Ser. No. 557,517, Jul. 24, 1990, abandoned, said Ser. No. 82,182, is a continuation of Ser. No. 746,121, Aug. 15, 1991, abandoned, which is a continuation-in-part of Ser. No. 585,471, Sep. 20, 1990, abandoned, which is a continuation-in-part of Ser. No. 455,611, Dec. 22, 1989, Pat. No. 5,322,770, said Ser. No. 880,478, is a continuation of Ser. No. 455,967, Dec. 22, 1989, abandoned, which is a continuation-in-part of Ser. No. 143,441, Jan. 12, 1988, abandoned, which is a continuation-in-part of Ser. No. 63,509, Jun. 17, 1987, Pat. No. 4,889,818, which is a continuation-in-part of Ser. No. 899,241, Aug. 22, 1996, abandoned.

[51] Int. Cl.$^6$ .................................................. C12N 9/10
[52] U.S. Cl. .................. 435/193; 435/240.1; 436/8; 436/86; 536/24.3; 536/24.33
[58] Field of Search ........................ 436/8, 18, 86; 435/240.1, 4, 6, 193; 252/1; 536/24.3–24.33

[56] References Cited

U.S. PATENT DOCUMENTS

| | | | |
|---|---|---|---|
| 4,133,717 | 1/1979 | Johnson et al. | 435/253.6 |
| 4,563,406 | 1/1986 | Ohbayashi et al. | 430/513 |
| 4,889,818 | 12/1989 | Gelfand et al. | 435/194 |
| 5,310,893 | 5/1994 | Erlich et al. | 536/24.31 |
| 5,422,242 | 6/1995 | Young | 435/6 |

FOREIGN PATENT DOCUMENTS

| | | |
|---|---|---|
| 0359006 | 3/1990 | European Pat. Off. |
| 9109944 | 7/1991 | WIPO |

OTHER PUBLICATIONS

Kallen et al., 1962, "The Occurrence of a New Pyrimidine Base Replacing Thymine in a Bacteriophage DNA: 5-Hydroxymethyl Uracil" J. Mol. Biol. 5:248–250.

Good et al., 1966, "Hydrogen Ion Buffers for Biological Research" Biochemistry 5(2):467–477.

Karkas et al., 1972, "Action of DNA Polymerase I of *Escherichia coli* With DNA–RNA Hybrids as Templates" Proc. Natl. Acad. Sci. USA 69(2):398–402.

Karkas, 1973, "Reverse Transcription by *Escherichia coli* DNA Polymerase I" Proc. Natl. Acad. Sci USA 70(12):3834–3838.

Leob et al., 1973, "Copy of Natural RNAs with E. coli DNA Polymerase I" Nature New Biology 242:66–69.

(List continued on next page.)

*Primary Examiner*—Paula K. Hutzell
*Assistant Examiner*—Rachel Heather Freed
*Attorney, Agent, or Firm*—George W. Johnston; Stacey R. Sias; Douglas A. Petry

[57] ABSTRACT

Methods are provided for the replication and amplification of RNA sequences by thermoactive DNA polymerases. In a preferred embodiment, high temperature reverse transcription is coupled to nucleic acid amplification in a one tube, one enzyme procedure using a thermostable DNA polymerase. Methods for eliminating carry over contamination of amplifications due to prior reverse transcription reactions are also provided. Reagents particularly suited for the methods of the present invention are provided.

6 Claims, 6 Drawing Sheets

OTHER PUBLICATIONS

Gulati et al., 1974, "Conditions for Using DNA Polymerase I as an RNA–Dependent Polymerase" Proc. Natl. Acad. Sci. USA 71(4):1035–1039.

Temin and Mizutani, Chapter 7, The Enzymes, "RNA Tumor Virus DNA Polymerases" Paul Boyer, Academic Press, Inc. London, 1974 ed.

Travaglini and Leob, "Ribonucleic Acid Dependent Deoxyribonucleic Acid Synthesis by *Escherichia coli* Deoxyribonucleic Acid Polymerase I. Characterization of the Polymerization Reaction" Biochemistry 13(15):3010–3017.

Perrin and Dempsey, Buffers for pH and Metal Ion Control, Chapter 7, Entitled "Metal Ion Buffers" pp. 94–108 New York, Chapman and Hall, 1974.

Chien et al., 1976, "Deoxyribonucleic Acid Polymerase From the Extreme Thermophile *Thermus aquaticus*" J. Bacteriology 127(3):1550–1557.

Houdebline, 1976, "Synthesis of DNA Complementary to the mRNAs for Milk Proteins by *E. coli* DNA Polymerase I" Nucleic Acids Res. 3(3):615–630.

Mizutani and Temin, 1976, "Incorporation of Noncomplementary Nucleotides at High Frequencies by Ribodeoxyvirus DNA Polymerases and *Escherichia coli* DNA Polymerase I" Biochemistry 15:1510–1516.

Travaglini et al., 1976, "Template Recognition and Chain Elongation in DNA Synthesis in Vitro" J. Mol. Biol. 106:605–621.

Kaledin et al., 1980, "Isolation and Properties of DNA Polymerase From Extremely Thermophilic Bacterium *Thermus aquaticus* YT1" Biokhimiya 45(4):644–651.

"Metal Ions in Genetic Information Transfer" in Advances in Inorganic Biochemistry vol. 3, pp. 26–29, 32–35, and 42–46, published by Elsevier North Holland Inc. New York, N.Y. Eds. Eichorn, Gunther, Louis and Marzill, Luigi, 1981.

Ruttimann et al., 1985, "DNA Polymerase From the Extremely Thermophilic Bacterium *Thermus thermophilus* HB–8" Eur. J. Biochem. 149:41–46.

Jones and Foulkes, 1989, "Reverse Transcription of mRNA by *Thermus aquaticus* DNA Polymerase" Nuc. Acids Res. 17(20):8387–8388.

Lawyer et al., 1989, "Isolation, Characterization, and Expression in *Escherichia coli* of the DNA Polymerase Gene From *Thermus aquaticus*" J. Biol. Chem. 264(11):6427–6437.

Shimomaye and Salvato, 1989, "Use of Avian Myeloblastosis Virus Revrse Transcriptase at High Temperature for Sequence Analysis of Highly Structured RNA" Gene Anal. Techn. 6:25–28.

Tabor and Richarson, 1989, "Effect of Manganese Ions on the Incorporation of Dideoxynucleotides by Bacteriophage T7 DNA Polymerase and *Escherichia coli* DNA Polymerase I" Proc. natl. Acad. Sci. USA 86:4076–4080.

Mocharla et al., 1990, "Coupled Reverse Transcription–Polymerase Chain Reaction (RT–PCR) as a Sensitive and Rapid Method for Isozyme Genotyping" Gene 93:271–275.

Shaffer et al., 1990, "Amplification, Detection, and Automated Sequencing of Gibbon Interleukin–2 mRNA by Thermus aquaticus DNA Polymerase Reverse Transcription and Polymerase Chain Reaction" Analytical Biochemistry 190:292–296.

Tse and Forget, 1990, "Reverse Transcription and Direct Amplification of Cellular RNA Transcripts by Taq Polymerase" Gene 88:293–296.

Kawasaki, 1989, "Amplification of RNA Sequences via Complementary DNA (cDNA)" Amplifications 3:4–6.

Krishnamoorthy and Nakon, 1991, "Free Metal Ion Depletetion by Good's Buffers", IV, Bicine 1:1 and 2:1 Complexes With Mg(II), Ca(II), Mn(II), Co(II), Ni(II), Cu(II), and Zn(II) J. Coord. Chem. 23:233–243.

Levy and Teebor, 1991, "Site Directed Substitution of 5–Hydroxymethyluracil for Thymine in Replicating oX–174am3 DNA via Synthesis of 5–Hydroxymethyl2'–Deoxyuridine–5'–Triphospate" Nuc. Acids Res. 19(12):3337–3343.

Lou et al., 1991, "Renin Gene Expression in Various Tissues Determined by Single–Step Polymerase Chain Reaction" Clin. Exp. Pharm. Physiology 18:357–362.

Myers and Gelfand, 1991, "Reverse Transcription and DNA Amplification by a *Thermus thermophilus* DNA Polymerase" Biochemistry 30:7661–7666.

Ponce and Micol. 1992, "PCR Amplification of Long DNA Fragments" Nuc. Acids Res. 20(3):623.

Brown, Basic Principles in Nucleic Acid Chemistry 2:41–45, Academic Press, New York, N.Y., 1974.

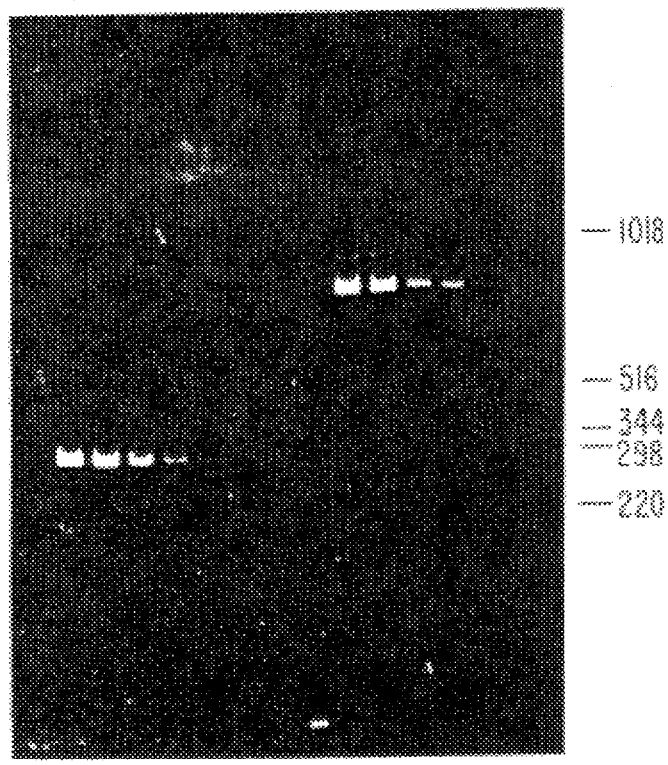
FIG._3

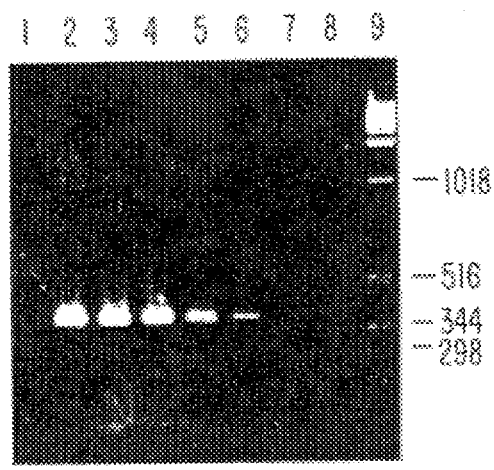
FIG._4
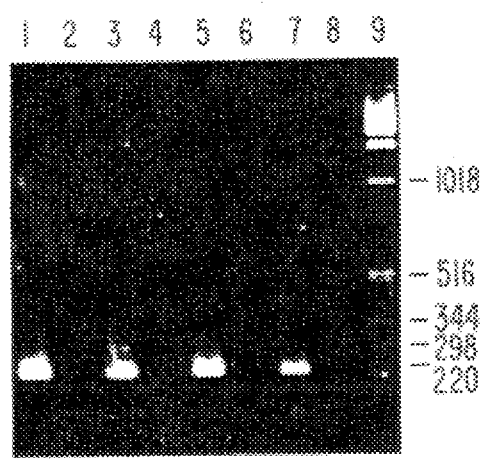
FIG._5

REAGENTS AND METHODS FOR COUPLED HIGH TEMPERATURE REVERSE TRANSCRIPTION AND POLYMERASE CHAIN REACTIONS

CROSS-REFERENCE

This is a continuation of application Ser. No. 08/086,483, filed Jul. 1, 1993 now abandoned which is a continuation-in-part (CIP) of Ser. No. 08/082,182, filed Jun. 24, 1993, now U.S. Pat. No. 5,310,652, which is a continuation of Ser. No. 07/746,121, filed Aug. 15, 1991, now abandoned, which is a CIP of PCT/US90/07641, filed Dec. 21, 1990, now abandoned, which is a CIP of Ser. No. 585,471, filed Sep. 20, 1990, now abandoned, which is a CIP of Ser. No. 455,611, filed Dec. 22, 1989 (now U.S. Pat. No. 5,322,770). Application Ser. No. 08/086,483 is also a CIP of Ser. No. 07/880,478, filed May 6, 1992, now abandoned which is a continuation of Ser. No. 455,967, filed Dec. 22, 1989, now abandoned, which is a CIP of Ser. No. 143,441, filed Jan. 12, 1988, (now abandoned) which is a CIP of Ser. No. 063,509, filed Jun. 17, 1987, which issued as U.S. Pat. No. 4,889,818, and which is a CIP of now abandoned Ser. No. 899,241, filed Aug. 22, 1986. Application Ser. No. 08/086,483 is also a CIP of Ser. No. 07/960,362, filed Jan. 5, 1993, (now U.S. Pat. No. 5,418,149) which is a CIP of Ser. No. 609,157, filed Nov. 2, 1990, now abandoned, which is a CIP of Ser. No. 557,517, filed Jul. 24, 1990 (now abandoned).

BACKGROUND OF THE INVENTION

1. Field of the Invention

The present invention relates to the field of molecular biology and provides improved methods for the replication and amplification of ribonucleic acid (RNA) sequences. In a preferred embodiment, the invention provides a method for synthesizing a complementary DNA copy from an RNA template with a thermoactive DNA polymerase. In another aspect, the invention provides methods for coupling reverse transcription of an RNA template and amplification of the resultant DNA using a thermostable DNA polymerase. In a preferred embodiment RNA is reverse transcribed and amplified in a homogeneous, one tube, one enzyme reaction. Methods for sterilization of reverse transcription and reverse transcription/amplification reactions are also provided.

2. Description of Related Art

The term "reverse transcriptase" describes a class of polymerases characterized as RNA-dependent DNA polymerases. All known reverse transcriptases require a primer to synthesize a DNA transcript from an RNA template. Historically, reverse transcriptase has been used primarily to transcribe mRNA into cDNA which can then be cloned into a vector for further manipulation.

Avian myoblastosis virus (AMV) reverse transcriptase was the first widely used RNA-dependent DNA polymerase (Verma, 1977, *Biochem. Biophys. Acta* 473:1). The enzyme has 5'-3' RNA-directed DNA polymerase activity, 5'-3' DNA-directed DNA polymerase activity, and RNase H activity. RNase H is a processive 5' and 3' ribonuclease specific for the RNA strand of RNA-DNA hybrids (Perbal, 1984, *A Practical Guide to Molecular Cloning*, Wiley & Sons New York). Errors in transcription cannot be corrected by reverse transcriptase because known vital reverse transcriptases lack the 3'→5' exonuclease activity necessary for proofreading (Saunders and Saunders, 1987, *Microbial Genetics Applied to Biotechnology*, Croom Helm, London). A detailed study of the activity of AMV reverse transcriptase and its associated RNase H activity has been presented by Berger et al., 1983, *Biochemistry* 22:2365–2372.

Berger et al. found that the rate limiting step in the reverse transcription of RNA was initiation by the enzyme, rather than the sequential polymerization of additional nucleotides. To overcome this limitation, use of stoichiometric, rather than catalytic, quantities of reverse transcriptase is frequently recommended (Buell et al., 1978, *J. Biol. Chem.* 253:2471–2482; Wickens et al., 1978, *J. Bio. Chem.* 253:2483–2495; Yoo et al., 1982, *Proc. Nat. Acad. Sci. USA* 80:1194–1198; and Okayama and Berg, 1982, *Mol. Cell. Biol.*2:161–170). However, when stoichiometric amounts of reverse transcriptase are used, the low level of RNase H activity is significant and may be responsible for fragmented cDNAs and limited cDNA yields (Kotewicz et al., 1988, *Nuc. Acid Res.* 16:265–277). Christopher et al., 1980, *Eur. J. Biochem.* 111:4190–4231, and Michelson et al., 1983, *Proc. Nat. Acad. Sci. USA* 80:472–476, have suggested that including an RNase inhibitor in cDNA reactions could alleviate this problem.

DNA polymerases isolated from mesophilic microorganisms such as *E. coli.* have been extensively researched (see, for example, Bessman et al., 1957, *J. Biol. Chem.* 2.33.:171–177 and Buttin and Kornberg, 1966, *J. Biol. Chem.* 241:5419–5427). *E. coli* DNA polymerase I (Pol I) is useful for a number of applications including: nick-translation reactions, DNA sequencing, in vitro mutagenesis, second strand cDNA synthesis, polymerase chain reactions (PCR), and blunt end formation for linker ligation (Maniatis et al., 1982, *Molecular Cloning: A Laboratory Manual* Cold Spring Harbor, N.Y.).

Several laboratories have shown that some DNA polymerases are capable of in vitro reverse transcription of RNA (Karkas, 1973, *Proc. Nat. Acad. Sci. USA* 70:3834–3838; Gulati et al., 1974, *Proc. Nat. Acad. Sci. USA* 71:1035–1039; and Wittig and Wittig, 1978, *Nuc. Acid Res.* 5:1165–1178). Gulati et al. found that *E. coli* Pol I could be used to transcribe Qβ viral RNA using oligo(dT)$_{10}$ as a primer. Wittig and Wittig have shown that *E. coli* Pol I can be used to reverse transcribe tRNA that has been enzymatically elongated with oligo(dA). However, as Gulati et al. demonstrated, the amount of enzyme required and the small size of the cDNA product suggests that the reverse transcriptase activity of *E. coli.* Pol I has little practical value.

The use of thermostable enzymes to amplify existing nucleic acid sequences in amounts that are large compared to the amount initially present was described in U.S. Pat. Nos. 4,683,195 and 4,683,202, which describe the polymerase chain reaction (PCR) processes. These patents are incorporated herein by reference. Primers, template, nucleoside triphosphates, the appropriate buffer and reaction conditions, and a polymerase are used in the PCR process, which involves denaturation of target DNA, hybridization of primers, and synthesis of complementary strands. The extension product of each primer becomes a template for the production of the desired nucleic acid sequence. These patents and U.S. Pat. No. 4,965,188, incorporated herein by reference, disclose that, if the polymerase employed is a thermostable enzyme, then polymerase need not be added after every denaturation step, because heat will not destroy the polymerase activity.

Thermostable DNA polymerases are not permanently inactivated even when heated to 93°–95° C. for brief periods of time, as, for example, in the practice of DNA amplification by PCR. In contrast, at this elevated temperature *E. coli* DNA Pol I and previously described reverse transcriptases are inactivated.

The thermostable DNA polymerase from *Thermus aquaticus* (Taq) has been cloned, expressed, and purified from recombinant cells as described in Lawyer et al., 1993, *PCR Methods and Applications*, 2:275–287; Lawyer et al., 1989, *J. Biol. Chem.* 264:6427–6437; and U.S. Pat. Nos. 4,889,818 and 5,079,352, which are incorporated herein by reference. Crude preparations of a DNA polymerase activity isolated from *T. aquaticus* have been described by others (Chien et al., 1976, *J. Bacteriol.* 127:1550–1557, and Kaledin et al., 1980, *Biokymiya* 45:644–651).

The thermostable DNA polymerase from *Thermus thermophilus (Tth)* has also been purified and is described in PCT Patent Publication No. WO 91/09950, which is incorporated herein by reference. PCT Patent Publication No. WO 91/09950 also describes that the gene encoding Tth DNA polymerase enzyme from *Thermus thermophilus* has been identified and cloned. Recombinant Tth provides an alternative means for preparing the thermostable enzyme. Crude preparations of DNA polymerase activity isolated from *T. thermophilus* have been described by Rüttimann et al., 1985, *Eur. J. Biochem.* 149:41–46. The thermostable DNA polymerase from *Thermotoga maritima* has been identified and cloned and is described in copending Ser. No. 567,244, filed Aug. 13, 1990, and PCT Pat. Publication No. WO 92/03556, which are incorporated herein by reference.

PCR requires a nucleic acid template and appropriate primers for amplification. The DNA to be amplified may be synthetic or genomic, contained in a plasmid, or contained in a heterogeneous sample. If the nucleotide sequence to be amplified is RNA, the nucleic acid molecule is first treated with reverse transcriptase in the presence of a primer to provide a cDNA template for amplification. Prior to the present invention, amplification of RNA necessitated a reverse transcription step with, e.g., a non-thermostable reverse transcriptase such as Molony Murine Leukemia Virus Reverse Transcriptase (MoMuLV RT) or AMV-RT, followed by treatment of the resulting single-stranded cDNA with a DNA polymerase. The amplification of RNA could be greatly simplified by the availability of a method for reverse transcribing RNA and amplifying DNA with a single enzyme.

Taq polymerase has been reported to inefficiently synthesize cDNA using $Mg^{+2}$ as the divalent metal ion (Jones and Foulkes, 1989, *Nuc. Acids. Res.* 176:8387–8388). Tse and Forget, 1990, *Gene* 88:293–296; and Shaffer et al., 1990, *Anal. Biochem.* 190:292–296, have described methods for amplifying RNA using Taq polymerase and $Mg^{+2}$ ion. However, the methods are inefficient and insensitive. For example, Tse and Forget demonstrate that 4 μg of total RNA is required to generate sufficient PCR product for ethidium bromide-stained gel visualization, using an abundantly expressed mRNA target. In addition, false positive signals from DNA template (PCR product from prior reactions or plasmid DNA contamination) were not rigorously excluded.

The present invention addresses this need and provides high temperature cDNA synthesis by thermoactive DNA polymerases. The present invention provides improved methods for a one enzyme, one tube, coupled reverse transcription/amplification assay using a thermostable DNA polymerase. The need to open the reaction vessel and adjust reaction components between the two steps is eliminated. The methods offer enhanced sensitivity, simplicity, and specificity over current methods.

SUMMARY OF THE INVENTION

In one aspect, the invention provides a method for amplifying a target RNA molecule in a sample, the method comprising the steps of: (a) treating the sample in a reaction mixture comprising a first and second primer, wherein the first primer is sufficiently complementary to the target RNA to hybridize therewith and initiate synthesis of a cDNA molecule complementary to the target RNA, and the second primer is sufficiently homologous to the target RNA to hybridize to the cDNA and initiate synthesis of an extension product, and a thermostable DNA polymerase in the presence of all four deoxyribonucleoside triphosphates, in an appropriate buffer, wherein the buffer comprises $Mn^{+2}$, at a temperature sufficient for the thermostable DNA polymerase to initiate synthesis of an extension product of the first primer to provide a cDNA molecule complementary to the target RNA; (b) treating the reaction mixture at an appropriate temperature to provide single-stranded cDNA; (c) treating the reaction mixture at an appropriate temperature for the thermostable DNA polymerase to initiate synthesis of an extension product of the second primer to provide a double-stranded cDNA molecule; and (d) amplifying the double-stranded cDNA molecule of step (c) by a polymerase chain reaction. In a preferred embodiment, the buffer comprises manganese acetate (also written $Mn(OAc)_2$ or $Mn(CH_3CO_2)_2$), Bicine-KOH (Bicine is N,N-Bis(2-Hydroxyethyl)glycine), and potassium acetate (also written KOAc or $KCH_3CO_2$).

The present invention provides methods for sterilizing reverse transcription reactions, amplification reactions, and homogeneous reverse transcription/amplification reactions, contaminated with nucleic acids generated from previous reverse transcription, amplification, and/or homogeneous reverse transcription/amplification reactions. For example the invention provides a method of sterilizing a reverse transcription reaction contaminated with nucleic acids generated from a previous reverse transcription wherein the previous reverse transcription resulted from mixing conventional and unconventional nucleoside triphosphates into a reverse transcription reaction mixture and generating cDNA products having the conventional and unconventional nucleotides incorporated therein, which method comprises degrading the contaminating nucleic acids by hydrolyzing covalent bonds of the unconventional nucleotides.

In another aspect, the invention provides a method of sterilizing a reverse transcription reaction contaminated with nucleic acids generated from a previous homogeneous reverse transcription/amplification reaction wherein the previous homogeneous reaction resulted from mixing conventional and unconventional nucleoside triphosphates into a homogeneous reverse transcription/amplification reaction mixture and generating cDNA and amplified products having the conventional and unconventional nucleotides incorporated therein, which method comprises degrading the contaminating amplified products by hydrolyzing covalent bonds of the unconventional nucleotides.

In one embodiment this method encompasses degrading the contaminating nucleic acid product with uracil-DNA glycosylase in an aqueous solution containing a target nucleic acid sequence; which further comprises inactivating the glycosylase in the presence of the target nucleic acid sequences (such as by heating); and, reverse transcribing and amplifying the target sequence by a thermostable DNA polymerase. The degradation of the contaminating product may be accomplished while the product is in contact with a nucleic acid reverse transcription/amplification reaction system. Thus, one can prepare a sample for reverse transcription/amplification, treat the sample by the present method to degrade any contaminating nucleic acid generated by a previous reverse transcription, amplification, and/or homogeneous reverse transcription/amplification reaction, and then amplify the target nucleic acid in the sample without having to adjust reaction volume or composition between steps.

In another aspect, the present invention provides reagents comprising a metal buffer which buffers the manganese ion concentration and which, in a preferred embodiment, buffers both the pH and the manganese ion concentration. The buffers significantly expand the usable range of manganese and dNTP concentrations in the methods of the present invention, thereby increasing the assay robustness and reducing problems with manganese chelators introduced during sample preparation. The buffers enable the use of higher dUTP concentrations in the sterilization methods of the present invention, which enhances dUTP incorporation in some targets and increases the efficiency of the sterilization by reducing the divalent metal ion concentration and lowering the ionic strength of the reaction mixture. The buffers also reduce the $Mn^{+2}$ catalyzed RNA hydrolysis, which enables longer reverse transcription times for the reverse transcription of rare and/or longer targets. Furthermore, the buffers and reagents (e.g., dNTPs) of the present invention are easier to produce because of the relaxed concentration tolerances and provide improved storage and stability characteristics. In a preferred embodiment of the invention the buffer comprises manganese acetate, Bicine-KOH, and potassium acetate.

BRIEF DESCRIPTION OF THE FIGURES

FIG. 3 depicts the results of the coupled RT/PCR assay described in Example V.

FIG. 4 depicts the results of the coupled RT/PCR assay described in Example VI using various amounts of total cellular RNA.

FIG. 5 depicts the results of an RT/PCR assay described in Example VII, wherein different thermostable enzymes are employed for the RT and PCR assays.

DETAILED DESCRIPTION

Figure 1:
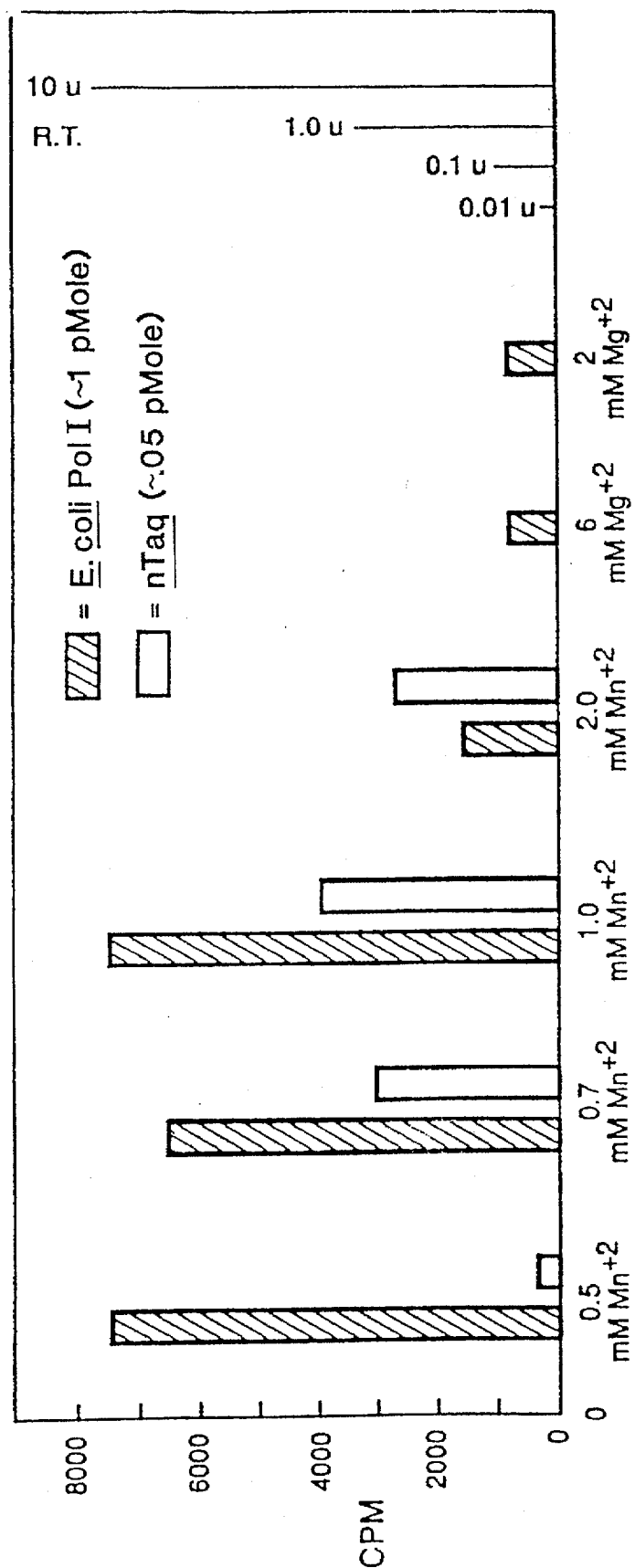
FIG. 1 is a graph comparing reverse transcriptase activity of E. coli Pol I, Taq and MoMuLV reverse transcriptase in $MgCl_2$ and $MnCl_2$ buffers.

The present invention provides improved methods for efficiently reverse transcribing and amplifying RNA. These improvements are achieved by the discovery and application of previously unknown properties of thermoactive DNA polymerases. The methods provide a one enzyme procedure for reverse transcribing and amplifying any desired RNA target and replace prior methods requiring more than one enzyme. Methods are provided for a coupled, one tube procedure that eliminates the need to open the reaction vessel for modifying reaction components between the reverse transcription and amplification steps. The invention also provides methods for minimizing the effects of carry-over contamination of RNA reverse transcription/ amplification assays due to reverse transcribed or amplified products from previous reactions. The invention also provides reagents which particularly enhance the methods of the present invention.

The methods comprise treating a sample containing said RNA template with an oligonucleotide primer, which primer is sufficiently complementary to said RNA template to hybridize therewith, and a thermoactive DNA polymerase in the presence of all four deoxyribonucleoside triphosphates, in an appropriate buffer and at a temperature sufficient for said primer to hybridize to said RNA template and said thermoactive DNA polymerase to catalyze the polymerization of said deoxyribonucleoside triphosphates to form a cDNA sequence complementary to the sequence of said RNA template. According to the invention, the DNA polymerase may be thermostable as well as thermoactive.

In another aspect, a primer suitable for annealing to an RNA template may also be suitable for amplification by PCR. For PCR, a second primer, complementary to the reverse transcribed cDNA strand, provides a site for initiation of synthesis of an extension product. As is well known, the thermostable DNA polymerase is able to catalyze this extension reaction on the DNA template; however, until the present invention, no one recognized that the enzyme could also catalyze the RNA-dependent reverse transcription reaction.

In the amplification of an RNA molecule by a thermoactive DNA polymerase, the first extension reaction is reverse transcription using an RNA template, and a DNA strand is produced. The second extension reaction, using the DNA template, produces a double-stranded DNA molecule. Thus, synthesis of a complementary DNA strand from an RNA template by a thermoactive DNA polymerase provides the starting material for amplification.

In another aspect of the invention, a thermostable DNA polymerase can be used in a coupled, one-enzyme reverse transcription/amplification reaction. Methods are provided for both non-homogeneous and homogeneous RT/PCR assays. The term "homogeneous" as used herein refers to a two-step single addition reaction for reverse transcription and amplification of an RNA target. By homogeneous it is meant that following the reverse transcription step, there is no need to open the reaction vessel or otherwise adjust reaction components prior to the amplification step. In a non-homogeneous RT/PCR reaction, following reverse transcription and prior to amplification any one or more of the reaction components is adjusted, added, or diluted including enzyme, primers, divalent cation, salts, pH, or dNTPs.

The term "homogeneous reverse transcription/ amplification reaction mixture" refers to an aqueous solution comprising the various reagents used to reverse transcribe and amplify a target RNA. These include enzymes, aqueous buffers, salts, oligonucleotide primers, target nucleic acid, and nucleoside triphosphates. Depending upon the context, the mixture can be either a complete or incomplete homogeneous reverse transcription/amplification reaction mixture.

The present invention provides simplified and improved methods for detecting RNA target molecules in a sample. These methods employ thermostable DNA polymerases to catalyze reverse transcription, second strand cDNA synthesis, and, if desired, amplification. Thus, the invention provides methods which require only one enzyme where previous methods required two. Prior methods also required two sets of incubation conditions, necessitated by the use of different enzymes for each procedure. The methods of the present invention provide RNA transcription and amplification with significantly enhanced specificity and with fewer steps than previous RNA cloning and diagnostic methods. These methods are adaptable for use in kits for laboratory or clinical analysis.

The term "reverse transcription reaction mixture" refers to an aqueous solution comprising the various reagents used to reverse transcribe a target RNA. These include enzymes, aqueous buffers, salts, oligonucleotide primers, target nucleic acid, and nucleoside triphosphates. Depending upon the context, the mixture can be either a complete or incomplete reverse transcription reaction mixture.

For amplification of the cDNA product a number of methods are available to one of ordinary skill in the art. As used herein the term "amplification reaction system" refers to any in vitro means for multiplying the copies of a target sequence of nucleic acid. Such methods include but are not limited to polymerase (PCR), DNA ligase (LCR), Qβ RNA replicase, and RNA transcription-based (TAS and 3SR) amplification systems. However, the homogeneous RT/PCR methods described herein have significant advantages over multi-step, multi-enzyme amplification methods such as 3SR in that only one polymerase enzyme is used.

Indeed, several different nucleic acid-based amplification systems can benefit from the considerable broadening of the divalent metal ion (e.g., $Mn^{+2}$) optima, and the surprising expansion of the distinctly different dual optima for RNA template-directed synthesis and DNA template-directed synthesis. All of these systems are based on the PCR process in that a product synthesized in one cycle or in a portion of a reaction serves as template in a succeeding cycle or in a succeeding portion of a reaction. In the Ligase Chain Reaction (LCR, Wu and Wallace, 1989, *Genomics* 4:560–569 and Barany, 1991, *Proc. Natl. Acad. Sci. USA* 88:189–193, which are incorporated herein by reference), four oligonucleotides are used to amplify an intended segment of DNA with a DNA ligase in the presence of $Mg^{+2}$ and necessary cofactors. Use of stringent annealing temperatures and a thermoactive and thermoresistant DNA ligase significantly improves the sensitivity of this process and the ability to discriminate allelic differences. Whether one uses a native thermophilic DNA ligase (e.g., Takahashi, Yamaguchi and Uchida, 1984, *J. Biol. Chem.* 259:10041–10047, incorporated herein by reference) or a recombinant thermophilic DNA ligase (e.g., Barany and Gelfand, 1991, *Gene* 109:1–11, incorporated herein by reference), the buffers and buffering agents of this invention are useful for broadening the metal ion optima, for facilitating both RNA template-directed ligation and DNA template-directed ligation, and for increasing the stability of RNA templates at elevated temperatures in the presence of divalent metal ions.

Similarly, nucleic acid amplification processes derived from PCR and LCR which use two or more enzymes (e.g., Polymerase Ligase Chain Reaction, Barany, 1991, *PCR Methods and Applic.* 1:5–16; or Gap-LCR, PCT Patent Publication No. WO 90/01069; or Repair Chain Reaction, European Patent Publication No. 439,182 A2, which are incorporated herein by reference) will benefit from the buffers and buffering agents of the present invention due to the broadening of the divalent metal ion optima for either or both RNA template-directed synthesis and DNA template-directed synthesis and to the increased stability of RNA templates at elevated temperatures in the presence of divalent metal ions. This is of particular advantage when the different nucleic acid interacting enzymes used in the process normally have different divalent metal ion optima.

Similarly, isothermal nucleic acid amplification processes (e.g., 3SR, Kwoh et al., 1989, *Proc Natl. Acad. Sci. USA* 86:1173–1177, Guatelli et al., 1990, *Proc Natl. Acad. Sci. USA* 87:1874–1878, PCT Patent Publication No. WO 92/0880A; NASBA, U.S. Pat. No. 5,130,238, which are incorporated herein by reference) that utilize multiple enzymes will benefit from this invention and the broadening of the divalent metal ion optima for either or both RNA template-directed synthesis and DNA template-directed synthesis. This is of particular advantage when the different nucleic acid interacting enzymes used in the process normally have different divalent metal ion optima. The isothermal amplification systems described above all utilize mesophilic or nonthermoactive and thermosensitive nucleic acid binding enzymes. Isothermal amplifications systems based on analogous thermoactive and thermoresistant enzymes (e.g., substitution of [1] *Thermus thermophilus* DNA polymerase for AMV or MoMuLV reverse transcriptase, [2] *Thermus thermophilus* RNase H [Itaya and Kondo, 1991, *Nuc. Acids Res.* 19:4443–4449 ] for *E. coli* RNase H and [3] *Thermus thermophilus* phage φYS40 [Sakaki and Oshima, 1975, *J. Virol.* 15:1449–1453] RNA polymerase for bacteriophage T3, T7 or SP6 RNA polymerases) will particularly benefit from the buffers and buffering agents of the present invention for the reasons stated above as well as the increased stability at elevated temperatures of RNA templates in the presence of divalent metal ions and the buffers and buffering agents of this invention.

This invention is not limited to any particular amplification system. As other systems are developed, those systems may benefit by practice of this invention. A recent survey of amplification systems was published in Abramson and Myers, 1993, *Current Opinion in Biotechnology* 4:41–47, incorporated herein by reference.

The term "amplification reaction mixture" refers to an aqueous solution comprising the various reagents used to amplify a target nucleic acid. These include enzymes, aqueous buffers, salts, amplification primers, target nucleic acid, and nucleoside triphosphates. Depending upon the context, the mixture can be either a complete or incomplete amplification reaction mixture. In the preferred embodiment of the invention the amplification system is PCR and the amplification reaction mixture is a PCR mixture.

The term "buffer," as used herein, refers to a solution containing a buffering agent or a mixture of buffering agents and, optionally, a divalent cation and a monovalent cation.

The present invention is suitable for transcribing and amplifying RNA from a number of sources. The RNA template may be contained within a nucleic acid preparation from an organism, for example, a viral or bacterial nucleic acid preparation. The preparation may contain cell debris and other components, purified total RNA, or purified mRNA. The RNA template may be a population of heterogeneous RNA molecules in a sample or a specific target RNA molecule.

RNA suitable for use in the present methods may be contained in a biological sample suspected of containing a specific target RNA. The biological sample may be a heterogeneous sample in which RNA is a small portion of the sample, as in for example, a blood sample or a biopsied tissue sample. Thus, the method is useful for clinical detection and diagnosis. The RNA target may be indicative of a specific disease or infectious agent.

RNA is prepared by any number of methods; the choice may depend on the source of the sample and availability. Methods for preparing RNA are described in Davis et al., 1986, *Basic Methods in Molecular Biology*, Elsevier, N.Y., Chapter 11; Ausubel et al., 1987, *Current Protocols in Molecular Biology*, Chapter 4, John Wiley and Sons, NY; Kawasaki and Wang, 1989, *PCR Technology*, ed. Erlich, Stockton Press NY; Kawasaki, 1990, *PCR Protocols: A Guide to Methods and Applications*, Innis et al. eds. Academic Press, San Diego; and Wang and Mark, 1990, *PCR Protocols: A Guide to Methods and Applications*, Innis et al. eds. Academic Press, San Diego; all of which are incorporated herein by reference.

In the illustrative embodiments, the RNA templates were synthesized in vitro by T7, T3, or SP6 RNA polymerase transcription from a DNA template. The resulting RNA molecule, referred to as cRNA, may be purified by various means including gel electrophoresis or oligo(dT) chromatography (see Wang et al., 1989, *Proc Natl. Acad. Sci.* 86:9717, and U.S. Pat. No. 5,219,727, incorporated herein by reference).

The first step of the present method requires that the RNA template is combined with a suitable primer. As used herein the term "primer" refers to an oligonucleotide capable of acting as a point of initiation of DNA synthesis when annealed to a nucleic acid template under conditions in which synthesis of a primer extension product is initiated, i.e., in the presence of four different nucleoside triphosphates and a thermostable enzyme in an appropriate buffer ("buffer" includes pH, ionic strength, cofactors, etc.) and at a suitable temperature. A suitable primer useful in step (a) of the disclosed methods can hybridize to an RNA template. A primer comprising a sequence sufficiently complementary to a specific RNA target molecule may be used to prime synthesis of the first cDNA strand complementary to a specific target RNA segment if present. The primer is sufficiently long to prime the synthesis of extension products in the presence of the thermostable enzyme. The primer may be an oligodeoxyribonucleotide such as oligo(dT).

Oligo(dT) hybridizes to the polyadenylation (polyA) sequence of mRNAs and provides a primer for cDNA synthesis from a heterogeneous population of mRNAs. Because most eukaryotic mRNA molecules contain a polyA sequence at the 3' end, an oligo(dT) primer has general utility in the present methods, for example, in the preparation of a cDNA library.

The primer typically contains 10–35 nucleotides, although the exact number is not critical to the successful application of the method. Short primer molecules generally require lower temperatures to form sufficiently stable hybrid complexes with the template. For oligo(dT), a primer 16–21 nucleotides in length is suitable for high temperature cDNA synthesis according to the disclosed methods; however, it may be preferable to provide an initial incubation at suboptimal temperature to elongate the oligo(dT) primer, thus providing enhanced stability of the primer-template duplex. For example, although Tth DNA polymerase has reduced activity at temperatures low enough for $d(T)_{16}$ to anneal, the enzyme has sufficient RT activity to extend $d(T)_{16}$ on an RNA template at 42° C. Thus, a preferred method for high temperature reverse transcription using $oligo(dT)_{16-21}$ includes a 5–10 minute room temperature incubation, generally carried out as part of setting up the reaction, followed by 10 minutes at 42° C. and finally 2.5–15 minutes at 70° C. Alternatively, low temperature incubations can be avoided by using oligo(dT) of increased chain length (i.e., $oligo(dT)_{35-45}$). In the Examples, primers are provided which are DNA and complementary to a portion of the mRNA molecules encoding the human cytokines interleukin-1-alpha (IL-1α) or interleukin-1-beta (IL-1β). In several examples, the cDNA primer hybridizes to a synthetic RNA template (cRNA). Other examples provide primers that hybridize to regions of the human immunodeficiency virus (HIV) and hepatitis C virus (HCV) genomes.

Synthetic oligonucleotides can be prepared using the triester method of Matteucci et al., 1981, *J. Am. Chem. Soc.* 103:3185–3191, incorporated herein by reference. Alternatively automated synthesis may be preferred, for example, on a Biosearch 8700 DNA Synthesizer using cyanoethyl phosphoramidite chemistry.

For primer extension to occur this primer must anneal to the RNA template. Not every nucleotide of the primer must anneal to the template for reverse transcription to occur. The primer sequence need not reflect the exact sequence of the template. For example, a non-complementary nucleotide segment may be attached to the 5' end of the primer with the remainder of the primer sequence being complementary to the RNA. Alternatively, non-complementary bases can be interspersed into the primer, provided that the primer sequence has sufficient complementarity with the RNA template for hybridization to occur and allow synthesis of a complementary DNA strand.

Prior methods of cDNA preparation required a pre-annealing step. Destabilization of secondary and tertiary structure of the RNA template may be required to allow the primer to hybridize to the RNA. Generally, annealing is accomplished by various means and is routinely accomplished in the presence of an annealing buffer. Maniatis et al. (supra) provide examples of annealing buffers. Annealing methods include, but are not limited to, incubating the RNA/primer mixture at a high temperature for a short period of time followed by step-wise cooling or quick chilling the mixture in a dry ice/ethanol bath. To prevent intra-strand secondary structure interactions from interfering with cDNA synthesis or primer annealing, at the low temperatures used previously for reverse transcription, some investigators modify the RNA template by treatment with chemical denaturants such as methylmercury hydroxide (Baily and Davidson, 1976, *Anal. Biochem.* 70:75, incorporated herein by reference). However, such denaturants are generally highly toxic, carcinogenic compounds and must be carefully removed to prevent enzyme inhibition.

According to the present invention, although the primer must anneal to the template for reverse transcription to occur, a separate annealing step is not a necessity. Because thermoactive reverse transcriptase activity is not irreversibly denatured at the high temperatures preferred for stringent annealing, there is no need for the quick chill or step-wise cooling of the denatured template, prior to the addition of the polymerase. Prior methods necessitated that the heated, denatured RNA was cooled in a manner that would maintain the annealed primer-template structure while reducing the temperature to provide conditions compatible with enzyme activity, usually 37°–42° C. The present invention provides methods for high temperature reverse transcription of RNA and eliminates the necessity of a pre-annealing step and the use of chemical denaturants. This aspect of the invention is exemplified in Examples V–XI. The present invention provides improved means for destabilizing RNA secondary and tertiary structure. The elevated temperatures for reverse transcription with a thermostable DNA polymerase further destabilize RNA secondary and tertiary structure and also serves to denature double-stranded RNA target.

The present methods provide that reverse transcription of the annealed primer-RNA template is catalyzed by a thermoactive or thermostable DNA polymerase. As used herein, the term "thermostable polymerase" refers to an enzyme that is heat stable or heat resistant and catalyzes polymerization of deoxyribonucleotides to form primer extension products that are complementary to a nucleic acid strand. Thermostable DNA polymerases useful herein are not irreversibly inactivated when subjected to elevated temperatures for the time necessary to effect destabilization of single-stranded nucleic acids or denaturation of double-stranded nucleic acids during PCR amplification. Irreversible denaturation of the enzyme refers to substantial loss of enzyme activity. Preferably a thermostable DNA polymerase will not irreversibly denature at about 90°–100° C. under polymerization conditions.

In another aspect of the invention, it is only essential that the DNA polymerase for high temperature reverse transcription is thermoactive. As used herein, the term "thermoactive polymerase" refers to an enzyme that is capable of efficiently catalyzing polymerization of deoxyribonucleotides to form a primer extension product complementary to a nucleic acid template strand at temperatures equal to or greater than 60° C. According to the present invention, thermoactive polymerases for reverse transcription have maximal activity over 50° C. The thermoactive DNA polymerase will not irreversibly denature at temperatures between 50°–80° C. under conditions for RNA destabilization and primer annealing.

In the examples provided, the thermoactive DNA polymerases are also thermostable; however, a thermoactive, non-thermostable enzyme is also suitable for practicing the present invention. Because the preparation of cDNA from an RNA template does not involve repeated denaturation cycles at elevated temperatures, it is not essential that enzymes useful in the method are thermostable as well as thermoactive. However, in one embodiment of the invention, a homogeneous RT/PCR procedure is provided. Because the reaction components are not adjusted between the RT and PCR steps, a thermostable DNA polymerase is preferred.

The heating conditions will depend on the buffer, salt concentration, and nucleic acids being denatured. Of course, it will be recognized that for the reverse transcription of mRNA, the template molecule is generally single-stranded and, therefore, a high temperature denaturation step is unnecessary. However, double-stranded RNA also provides a suitable template for the reverse transcription/ amplification methods described, following an initial denaturation or strand-separation step. The present invention provides buffers which decrease RNA degradation at the high temperatures required for heat denaturation of double-stranded RNA, thereby improving the efficiency of reverse transcription/amplification reactions from double-stranded RNA templates. The buffers of the present invention permit brief, very high temperature treatment of the complete reaction mixture to further destabilize any RNA secondary and tertiary structure immediately prior to the primer annealing step of the reverse transcription reaction (Example XIX). Double-stranded RNA templates may include, for example, Reo virus, blue tongue virus, Colorado tick fever virus, and yeast killer factor.

Temperatures for RNA destabilization typically range from 50°–80° C. A first cycle of primer elongation provides a double-stranded template suitable for denaturation and amplification as referred to above. Temperatures for nucleic acid denaturation typically range from about 90° to about 100° C. for a time sufficient for denaturation to occur, which depends on the nucleic acid length, base content, and complementarity between single-strand sequences present in the sample, but typically about 10 seconds to 4 minutes.

The thermostable or thermoactive DNA polymerase preferably has optimum activity at a temperature higher than about 40° C., e.g., 60°–80° C. At temperatures much above 42° C., DNA and RNA-dependent polymerases, other than thermostable or thermoactive DNA polymerases, are inactivated. Shimomave and Salvato, 1989, *Gene Anal. Techn.* 6:25–28, incorporated herein by reference, describe that at 42° C. AMV-RT has maximum activity. At 50° C. the enzyme has 50% activity, and at 55° C. AMV-RT retains only 10% of its optimal level of activity. Thus, AMV-RT is inappropriate for catalyzing high temperature polymerization reactions utilizing an RNA template. Only the present method provides methods for efficient high temperature reverse transcription with thermoactive DNA polymerases.

Hybridization of primer to template depends on salt concentration as well as composition and length of primer. When using a thermostable or thermoactive polymerase, hybridization can occur at higher temperatures (e.g., 45°–70° C.) which are preferred for increased selectively and/or higher stringency of priming. Higher temperature optimums for the polymerase enzyme enable RNA reverse transcription and subsequent amplification to proceed with greater specificity due to the selectivity of the primer hybridization process. Preferably, the optimum temperature for reverse transcription of RNA ranges from about 55°–75° C., more preferably 60°–70° C.

The present invention provides a method for reverse transcription of an RNA template, having enhanced primer-directed specificity, catalyzed by a thermostable DNA polymerase. The methods disclosed are improved over prior methods for the reverse transcription of RNA. These methods provide for the amplification of an RNA segment via an RNA/cDNA hybrid intermediate molecule. The hybrid molecule is a suitable template for amplification by PCR. Thus, the reverse transcription and amplification reactions are coupled. Previous RNA amplification methods require incubation of the RNA/primer mixture in the presence of reverse transcriptase at 37°–42° C. prior to the initiation of an amplification reaction. Only by the present invention are all of the enzymatic steps for RNA amplification catalyzed by a thermostable DNA polymerase. The advantages brought to PCR by the commercial availability of Taq and Tth DNA polymerases, the disclosed methods for preparing Tth DNA polymerase, and the commercial availability of Tth DNA polymerase reverse transcription/DNA amplification kits (Perkin Elmer, Norwalk, Conn.) are now, by the methods disclosed herein, applicable to reverse transcription, RNA detection, cDNA preparation and coupled reverse transcription/cDNA amplification of RNA.

DNA amplification procedures by PCR are well known and are described in U.S. Pat. Nos. 4,683,195, 4,683,202, and 4,965,188, each of which is incorporated herein by reference. For ease of understanding the advantages provided by the present invention, a summary of PCR is provided. PCR requires two primers that hybridize with the double-stranded target nucleic acid sequence to be amplified. In PCR, this double-stranded target sequence is denatured and one primer is annealed to each strand of the denatured target. The primers anneal to the target nucleic acid at sites removed from one another and in orientations such that the extension product of one primer, when separated from its complement, can hybridize to the other primer. Once a given primer hybridizes to the target sequence, the primer is extended by the action of a DNA polymerase. The extension product is then denatured from the target sequence, and the process is repeated.

In successive cycles of this process, the extension products produced in earlier cycles serve as templates for DNA synthesis. Beginning in the second cycle, the product of amplification begins to accumulate at a logarithmic rate. The amplification product is a discrete double-stranded DNA molecule comprising: a first strand which contains the sequence of the first primer, eventually followed by the sequence complementary to the second primer, and a second strand which is complementary to the first strand.

Due to the enormous amplification possible with the PCR process, small levels of DNA carryover from samples with high DNA levels, positive control templates or from previous amplifications can result in PCR product, even in the absence of purposefully added template DNA. If possible, all reaction mixes are set up in an area separate from PCR product analysis and sample preparation. The use of dedicated or disposable vessels, solutions, and pipettes (preferably positive displacement pipettes) for RNA/DNA preparation, reaction mixing, and sample analysis will minimize cross contamination. See also Higuchi and Kwok, 1989, Nature, 339:237–238 and Kwok, and Orrego, in: Innis et al. eds., 1990 PCR Protocols; A Guide to Methods and Applications, Academic Press, Inc., San Diego, Calif., which are incorporated herein by reference.

One particular method for minimizing the effects of cross contamination of nucleic acid amplification is described in PCT Patent Publication No. WO 92/01814 and U.S. Pat. No. 5,035,996, which are incorporated herein by reference. The method involves the introduction of unconventional nucleotide bases, such as dUTP, into the amplified product and exposing carryover product to enzymatic and/or physical-chemical treatment to render the product DNA incapable of serving as a template for subsequent amplifications. For example, uracil-DNA glycosylase, also known as uracil-N-glycosylase or UNG, will remove uracil residues from PCR product containing that base. The enzyme treatment results in degradation of the contaminating carryover PCR product and serves to "sterilize" the amplification reaction.

The term "unconventional" when referring to a nucleic acid base, nucleoside, or nucleotide includes modifications, derivations, or analogs of conventional bases, nucleosides or nucleotides which naturally occur in a particular polynucleotide (e.g., DNA [dA, dG, dC, dT] or RNA [A, G, C, U]). Uracil is a conventional base in RNA (i.e., covalent attachment to ribose in a ribopolynucleotide) but an unconventional base in DNA (i.e., covalent attachment to deoxyribose in a deoxyribopolynucleotide). In a coupled RT/PCR reaction, it is desirable to sterilize the reaction prior to the RT step to eliminate carryover nucleic acid products of prior reverse transcription and/or amplification reactions. Sterilization after reverse transcription, and prior to PCR, results in degradation of non-contaminating cDNA products containing dUTP, as well as contaminating product. Synthesis of cDNA in the presence of dTTP and absence of dUTP is impractical. For efficient incorporation of dUTP into the subsequent PCR product, a vast excess of dUTP would be required to dilute the dTTP present as carryover from the reverse transcription step. Furthermore, this would require opening the tube in order to add the dUTP. Consequently, the effectiveness of UNG sterilization would be diminished.

The present invention provides methods for sterilization of the RT/PCR reaction. Example XI demonstrates this aspect of the invention. When unconventional nucleosides are being incorporated into amplification products, routine titration experiments are useful to optimize reaction conditions, and U.S. Ser. No. 07/880,629, filed May 8, 1992, provides guidance for incorporating unconventional nucleotides. The parameters which are varied include, but are not limited to the concentration of divalent cation, pH range, concentration of DNA polymerase, concentration of the unconventional nucleoside, the addition of natural nucleoside for which the unconventional nucleoside is inserted, time of each cycle, and temperature.

Generally, the concentration of dNTPs in a PCR using $MgCl_2$ in a Tris buffer is within the range 20–200 μM for each dNTP. For incorporating dUTP the efficiency of amplification is improved at an elevated nucleotide concentration. In Example XI, the concentration of dUTP in the PCR is 200 μM and dCTP, dGTP, and dATP are also present at the same concentration, although this is not essential. When the concentration of dUTP or dNTPs is increased, the concentration of $MgCl_2$ and $MnCl_2$ is increased accordingly. In Example XI, the PCR contains 200 μM of each dGTP, dATP, dUTP, and dCTP and 2 mM $MgCl_2$, and provides efficient amplification.

For reverse transcription using a thermostable polymerase, $Mn^{+2}$ is preferred as the divalent cation and is typically included as a salt, for example, manganese chloride ($MnCl_2$), manganese acetate ($Mn(OAc)_2$), or manganese sulfate ($MnSO_4$). If $MnCl_2$ is included in a reaction containing 10 mM Tris buffer, for example, the $MnCl_2$ is generally present at a concentration of 0.5–7.0 mM; 0.8–1.4 mM is preferred when 200 μM of each dGTP, dATP, dUTP, and, dCTP are utilized; and 1.2 mM $MnCl_2$ is most preferred. The present invention provides methods and reagents to expand the usable range of the divalent cation concentration. In one embodiment of the invention, a reaction buffer comprising $Mn(OAc)_2$, Bicine-KOH, and KOAc is used in place of the $MnCl_2$, Tris, KCl buffer. Example XV describes the use of such a bicine/acetate buffer in which the $Mn^{+2}$, supplied as $Mn(OAc)_2$, is used at concentrations ranging from 1.2 to 2.5 mM; concentrations of 3.6 mM and 3.5 mM are utilized in the RT/PCR described in Example XVII.

The optimal concentrations of the unconventional nucleotide and divalent cation may vary in the reverse transcription reaction, just as for the amplification reaction as noted above, depending on the total dNTP concentration and on the particular primers, template, buffer, salts, and polymerase present. The examples describe the use of a bicine/acetate buffer which allows a higher concentration of dUTP in the reverse transcription reaction, thereby enhancing the incorporation of dUMP into newly the synthesized cDNA.

In one embodiment of the invention, described in Example X, a two step, single addition procedure is provided for coupled RT/PCR using $MnCl_2$ as the divalent cation in a Tris-HCl buffer for both the RT and PCR steps. In the method, following reverse transcription, no buffer adjustment is made prior to the PCR step. Consequently, a lower concentration of $MnCl_2$ is used, whether incorporating dTTP or dUTP (using 200 μM dNTPs), to avoid a reduction in amplification efficiency that may occur when $MnCl_2$ concentration is maintained at 1.2 mM during PCR.

Following amplification and analysis of the RT/PCR result, the RT/PCR product may be introduced unintentionally as a contaminant in other reactions. Prior to subsequent RT, RT/PCR or amplification reactions, the reaction mixtures are treated with a DNA glycosylase specific for the unconventional nucleotide incorporated during the prior RT/PCR. In this manner, any previous RT/PCR product, present as a contaminant in subsequent RT, RT/PCR or amplification reaction mix containing a target nucleic acid, is hydrolyzed.

Consequently, in practice, the sterilization treatment is carried out prior to the RT/PCR assay to eliminate carryover of dUMP containing product DNAs. For example, prior to the high temperature (60°–70° C.) incubation of the reverse transcription reaction mix, 0.01–0.05 units UNG per μl of RT reaction volume is added and incubated for 1–10 minutes at room temperature. Alternatively, the incubation is carried out for 2 minutes at 50° C. The subsequent high temperature (60°–70° C.) RT and 95° C. denaturation steps serve to inactivate UNG so that newly synthesized cDNA and PCR products are not degraded. UNG is commercially available from Perkin Elmer, Norwalk, CT. U.S. Ser. No. 07/880,629, incorporated herein by reference, describes methods for producing UNG by recombinant means and also thermolabile UNG derivatives which do not regain activity after heating above the denaturation temperature of the DNA sample. Such derivatives may be preferred for practicing the present invention.

The target of amplification can be an RNA/DNA hybrid molecule. The target can be a single-stranded or double-stranded nucleic acid. Although the PCR procedure described above assumed a double-stranded target, this is not a necessity. After the first amplification cycle of a single-stranded DNA target, the reaction mixture contains a double-stranded DNA molecule consisting of the single-stranded target and a newly synthesized complementary strand. Similarly, following the first amplification cycle of an RNA/cDNA target, the reaction mixture contains a double-stranded cDNA molecule. At this point, successive cycles of amplification proceed as described above. In the present methods, the target of amplification is a single-stranded RNA, and the first amplification cycle is the reverse transcription step. Alternatively, if the starting template is double-stranded RNA, an initial high temperature denaturing step may be used to prepare single-stranded RNA template.

As used herein the term "cDNA" refers to a complementary DNA molecule synthesized using a ribonucleic acid strand (RNA) as a template. The RNA may be mRNA, tRNA, rRNA, or another form of RNA, such as viral RNA. The cDNA may be single-stranded, double-stranded or may be hydrogen-bonded to a complementary RNA molecule as in an RNA/cDNA hybrid.

The methods of the present invention provide means for obtaining cDNA from a desired RNA template wherein the desired end product is produced with greater specificity than by previous methods. Additionally, the present invention provides that cDNA synthesis can be coupled to amplification by PCR. These methods incorporate previously unknown properties of thermoactive DNA polymerases. In the disclosed embodiments, methods are provided which utilize Taq and Tth DNA polymerases for reverse transcription. These embodiments should not be construed as a limitation of the present invention.

Thermostable polymerases are available from a number of sources. The enzyme may be a native or recombinant protein. A preferred thermostable enzyme is *Thermus thermophilus* DNA polymerase (Tth DNA polymerase), purified from *Thermus thermophilus* (see PCT Patent Publication No. WO 91/09950, which is incorporated herein by reference). Alternatively, Tth DNA polymerase is purified from recombinant host cells as described herein and may be designated as rTth DNA polymerase. Also preferred for practicing the invention is Taq DNA polymerase. Taq DNA polymerase is commercially available as a recombinant product or purified as native Taq DNA polymerase from *Thermus aquaticus* developed and manufactured by Hoffmann-La Roche Inc. and commercially available from Perkin Elmer, Norwalk, Conn. As used herein, recombinant Taq DNA polymerase may be designated as rTaq DNA polymerase and native Taq DNA polymerase may be designated as nTaq DNA polymerase. In addition, *T. flavus* (Tfl) DNA polymerase, available from Amersham, Arlington Heights, Ill., as "Hot Tub" DNA polymerase may be suitable.

An important aspect of the present invention relates to Tth DNA polymerase for reverse transcription and amplification of nucleic acids. Tth DNA polymerase is developed and manufactured by Hoffmann-La Roche Inc. and commercially available from Perkin Elmer, Norwalk, Conn. The gene encoding this enzyme has been cloned from *T. thermophilus* genomic DNA. Tth polymerase has a predicted molecular weight of about 94 kDa, based on the inferred amino acid sequence. The complete coding sequence (~2.5 kb) for the Tth polymerase can be easily obtained in an ~3.7 kilobase (kb) HindIII-BstEII restriction fragment of plasmid pBSM:Tth, although this ~3.7 kb fragment contains an internal HindIII restriction enzyme site. One specific isolate of pBSM:Tth in *E. coli* K12 strain DG101 was purified and referred to as pBSM:Tth10. This plasmid was deposited with the American Type Culture Collection (ATCC) in host cell *E. coli* K12 strain DG101 on Dec. 21, 1989, under ATCC accession No. 68195. The availability of the Tth DNA polymerase gene sequence provides the necessary starting material for one skilled in the art to prepare any number of expression vectors applicable to a variety of host systems for preparing recombinant Tth DNA polymerase. Similarly, mutant forms of the polymerase may be prepared that retain the DNA polymerase activity and are within the meaning of the term *Thermus thermophilus* DNA polymerase.

A number of Tth DNA polymerase expression vectors are described in PCT Patent Publication No. WO 91/09950, which are suitable for producing recombinant purified Tth for use in the present invention, and that application is incorporated herein by reference. Of these expression vectors, plasmid pLSG33 *E. coli* K 12 strain DG 116 was used as a source of recombinant Tth. In plasmid pLSG33, expression of the gene encoding Tth polymerase is regulated by the $\lambda P_L$ promoter. Construction of pLSG33 is described in detail in PCT Patent Publication No. WO 91/09950, and incorporated herein by reference. In that description pBSM:Tth is utilized as the source of the Tth gene.

Once the Tth DNA polymerase has been expressed in a recombinant host cell, the enzyme can be purified and used in the methods disclosed herein. Purification procedures have been previously described for native Tth and native and recombinant Taq DNA polymerase in Ser. No. 455,611, filed Dec. 22, 1989, and U.S. Pat. No. 5,079,352, incorporated herein by reference. Purification of recombinant Tth DNA polymerase is generally similar, and the previously described processes are suitable. However, a preferred method for purifying recombinant Tth DNA polymerase is provided in Example I in the present specification. The procedure for purifying recombinant Tth DNA polymerase is simplified over the native Tth DNA polymerase purification scheme. Because the non-native host cell does not produce TthHB8 endonuclease I, which co-elutes with native Tth DNA polymerase, the steps taken to remove TthHB8I endonuclease are not needed.

Although the present invention is exemplified by Taq and Tth DNA polymerases, the invention is not limited to that description. Other thermostable polymerases that have been reported in the literature will also find use in the practice of the methods described. Examples of these include polymerases extracted from the thermophilic bacteria *Bacillus stearothermophilus, Thermosipho africanus, Thermotoga maritima*, Thermus species SPS17, *T. flavus, T. lacteus, T.* rubens, T. ruber, and T. species Z05. In addition, thermostable polymerases isolated from the thermophilic archae include, for example, *Desulfurococcus mobilis, Methanobacterium thermoautorophicum, Methanothermus fervidus, Pyrrococcus furiosus, Pyrodictium occultum, Sulfolobus acidocaldarius, S. solfataricus, Thermococcus litoralis, Thermoplasma acidophilum,* and *Pyrodictium abyssi.*

Modified thermostable polymerases may result from proteolytic degradation or may be produced from a truncated gene. These proteins are also useful in the practice of the present invention so long as they function to polymerize deoxyribonucleoside triphosphates using an RNA template.

Taq DNA polymerase can be prepared as both a 94 kDa and 61 kDa enzyme. The 61 kDa enzyme has been previously referred to as the 62 kDa enzyme (see, for example, Lawyer et al., 1993, supra., and U.S. Pat. Nos. 4,889,818 and 5,079,352) and may be referred to as the Stoffel Fragment; however, the Taq 61 kDa, 62 kDa, and Stoffel Fragment enzyme all refer to the same identity. The Stoffel Fragment enzyme is a processed form of the 94 kDa enzyme, resulting from proteolytic cleavage of the N-terminal region. Alternatively, the Stoffel fragment enzyme can be made directly as a recombinant protein. The Stoffel Fragment is composed of approximately two-thirds of the carboxy-terminal portion of the full length protein. Either form of the enzyme will function to reverse transcribe RNA as described herein. In addition to the N-terminal deletion, individual amino acid residues may be modified by oxidation, reduction, or other derivatization, or the protein may be cleaved to obtain fragments that retain activity.

Thus, modification to the primary structure itself by deletion, addition, or alteration of the amino acids incorporated into the sequence during translation can be made without destroying the high temperature DNA polymerase activity of the protein. Such substitutions or other alterations result in proteins useful in the methods of the present invention. The availability of DNA encoding these sequences provides the opportunity to modify the codon sequence to generate mutant protein forms also having reverse transcriptase activity.

As demonstrated herein, Tth DNA polymerase has high reverse transcriptase activity. However, Tth DNA polymerase, as well as Taq DNA polymerase, lacks a 3' to 5' exonucleolytic proofreading activity. This 3' to 5' exonuclease activity is generally considered to be desirable in certain applications because it allows removal of misincorporated or unmatched bases in the newly synthesized nucleic acid sequences. Because the lack of a proofreading activity may effect enzyme fidelity, the presence of a proofreading exonuclease would be a novel and potentially useful property for a reverse transcriptase.

*Thermotoga maritima* DNA polymerare (Tma pol) has 3' to 5' exonuclease activity. U.S. patent application Ser. No. 567,244, filed Aug. 13, 1990, and PCT Patent Publication No. WO 92/03556 provide means for isolating and producing Tma DNA polymerase. That patent application provides the amino acid and nucleic acid sequences for Tma DNA polymerase and describes the amino acid domains for various enzyme activities, including the 3' to 5' exonuclease activity, as well as the 5' to 3' exonuclease activity.

Accordingly, domain shuffling or construction of chimeric DNA polymerases may be used to provide thermostable DNA polymerases containing novel properties. For example, a thermostable chimeric DNA polymerase which has the 3' to 5' exonuclease domain of Tma polymerase incorporated into Tth polymerase can be constructed using "overlap" PCR (Higuchi, 1989, *PCR Technology* supra.). In this method, the intended junction sequence is designed into the PCR primers (at their 5' ends). Following the initial amplification of each individual domain, the various products are diluted (ca. 100- to 1,000-fold) and combined, denatured, annealed, extended, and then the final forward and reverse primers are added for an otherwise standard PCR.

Specifically, the polymerase domain of Tth DNA polymerase (amino acids 415–834) is joined to the 5' to 3' and 3' to 5' exonuclease domains of Tma DNA polymerase (amino acids 1–475). For example, a Tth DNA polymerase expression vector and a portion of the gene encoding Tma DNA polymerase can be combined as follows. The expression vector pLSG33 is described PCT Patent Publication No. WO 91/09950 and contains a modified gene encoding Tth DNA polymerase. Plasmid pTMA5'∇Nde#3 (subsequently referred to as pTma06), described in co-pending U.S. Ser. No. 567,244, filed Aug. 13, 1990, which is incorporated herein by reference, contains the 5' portion of the gene encoding Tma DNA polymerase. To prepare the plasmid for overlap PCR, the pLSG33 and pTma06 are linearized with NdeI and used in two separate PCR amplifications using primers A and B for the 5'-portion of the Tma DNA polymerase, and primers C and D for the 3'-portion of the Tth DNA polymerase. The primers' sequences are:

| A | SEQ ID No. 1 | 5'-GGCATATGGCTAGACTATTTCTTTTTG-3' |
| B | SEQ ID No. 2 | 5'-AGGTTCCGATGAAGTCTGTAGGTGATGTCTG-3' |
| C | SEQ ID No. 3 | 5'-CTACAGACTTCATCGGAACCTCCTTAAGCG-3' |
| D | SEQ ID No. 4 | 5'-CCAACCCGCCTCGGCCACGAAGG-3' |

In addition to the region of complementarity designed into primers B and C, primer A has an NdeI site incorporated into its 5'-terminus. Primer D corresponds to a portion of the polymerase domain of Tth and is directly distal to a BamHI site within the 3' region of the Tth gene. The first round of PCR generates product AB (1441 base pair [bp]) and product CD (586 bp). Following the initial amplification of the individual domains, the reactions are diluted approximately 100- to 1000-fold and combined, denatured, annealed, and extended using the final forward and reverse primers (primers A and D, respectively). The final product, AD, is digested with NdeI and BamHI to provide a 2006 bp product. This product is then ligated back into the expression vector (following digestion of the vector, pLSG33, with NdeI and BamHI) and transformed into an appropriate host. The chimeric protein will contain 895 amino acid residues.

Tth, Taq, and Tma DNA polymerases also contain a 5' to 3' exonuclease activity which may be responsible for RNase H activity. The elimination or reduction of 5' to 3' exonuclease activity by, for example, site specific mutagenesis, may provide a preferred form of thermostable DNA polymerase for cDNA synthesis. A substitution of glutamic acid for a glycine residue at amino acid number 103 of the pol A gene of *E. coli* has been demonstrated to produce a polypeptide defective in 5' to 3' exonuclease activity (Kingsbury and Helinski, 1973, *J. Bacteriol.* 114: 1116–1124; Olivera and Bonhoeffer, 1974, *Nature* 250: 513–514; and Joyce et al., 1985, *J. Mol. Biol.* 186: 283–293, all of which are incorporated herein by reference). The homologous amino acid is conserved in Tth DNA polymerase (amino acid number 108). The normal GGG codon is mutated to a GAA codon by PCR to provide a novel thermostable DNA polymerases with improved characteristics for reverse transcription of RNA. Alternatively, changing Tth amino acid number 46 from glycine to aspartic acid can affect the 5'→3' exonuclease activity providing a novel enzyme (PCT Patent Publication No. WO 92/06200, incorporated herein by reference).

The fidelity of viral reverse transcriptases, such as AMV-RT and MoMuLV-RT, is compared to thermoactive reverse transcriptases by a straightforward assay procedure. Plasmid BS+ (Stratagene) is used for such an assay. The plasmid encodes an α-complementing β-galactosidase activity and can be linearized with NdeI. T3 RNA polymerase is used to prepare a cRNA transcript of the α-donor region. After treatment of the cRNA with RNase-free DNase and isolation of the cRNA, the cRNA is used as a template for a reverse transcription/amplification reaction. A reverse transcription primer complementary to the 3' end of the cDNA containing an NdeI sequence at its 5' terminus, and an upstream PCR primer comprising a PstI sequence at the 5' termini provide a 752 bp PCR product. The PCR product and the pBS+ vector are then digested with NdeI and PstI followed by ligation of the PCR product into the vector and transformation into a suitable host. The presence of white colonies indicates that a mutation had occurred during the RT or PCR amplification. The assay provides means for assigning a relative value to the fidelity of the reverse transcriptase activity of various enzymes. Specific mutations can be determined by sequence analysis.

The method of high temperature reverse transcription provides novel means for the detection of specific RNAs in a sample. This method is useful in a clinical setting to monitor, for example, retrovirus infection in children born to AIDS victims or to monitor the expression of diagnostic proteins. Detection of the reverse transcribed or amplified products can be accomplished by any of a number of known means. Such means include, but are not limited to, hybridization with isotopic or non-isotopically labeled probes in, for example, a dot blot or electrophoretic format. A detection format may include a capture step, such as a solid support substrate and avidin-biotin label system. U.S. Pat. No. 5,210,015, incorporated herein by reference, describes a method for use of the 5' to 3' nuclease activity of a nucleic acid polymerase. According to the method, a labeled nucleic acid probe in a hybridized duplex composed of a labeled oligonucleotide and a target oligonucleotide is degraded. Labeled fragments are subsequently detected. Detection may also include quantitative analysis to monitor progress of, for example, an infection or response to a treatment regimen. Alternatively, detection may be for the purpose of cell typing.

Primers can be designed with convenient restriction enzyme recognition sequences located at or near the 5' end of the primer. In the formation of the cDNA transcript, so long as the 3' end of the primer is hydrogen-bonded to the target sequence, the resulting double-stranded cDNA molecule would contain a specific restriction enzyme recognition sequence. Following amplification, using the cDNA as a template, the restriction site could be used to facilitate other procedures, for example, cloning.

Following reverse transcription of RNA by a thermoactive or thermostable DNA polymerase, the RNA can be removed from the RNA/cDNA hybrid by heat denaturation or by a number of other known means such as alkali, heat, or enzyme treatment. Enzyme treatment may consist of, for example, treating the RNA/cDNA hybrid with RNase H. RNase H is specific for RNA strands within an RNA/DNA double-stranded molecule. Tth and Taq associated RNase H and 5'→3' nuclease activities can facilitate hydrolysis of the RNA template and synthesis of the second DNA strand, as well as primer extension for amplification of the cDNA sequence. Alternatively, exogenous RNase H is added from a commercially available source.

The RNase H activity of thermostable polymerases provides means for distinguishing between RNA and DNA templates in a sample. This is particularly useful for detecting RNA in the presence of homologous duplex DNA. Where the DNA is free of introns in, for example, proviral HIV DNA, amplified RNA, and DNA may not be distinguishable by size. However, following reverse transcription, thermostable RNase H activity eliminates the necessity for denaturating the RNA/cDNA duplex. Consequently, in the presence of genomic or proviral DNA, only the RNA template is amplified in the first PCR cycle.

In a preferred method for distinguishing between homologous RNA and DNA templates, amplification primers are used to direct the synthesis of the PCR product with a low strand separation temperature. For example, for detecting HIV RNA, primer pairs:

| Primer | SEQ ID No. | Sequence |
| --- | --- | --- |
| SK462 | 5 | 5'-AGTTGGAGGACATCAAGCAGCCATGCAAAT-3' |
| SK431 | 6 | 5'-TGCTATGTCAGTTCCCCTTGGTTCTCT-3' |
| SK38 | 7 | 5'-ATAATCCACCTATCCCAGTAGGAGAAAT-3' |
| SK39 | 8 | 5'-TTTGGTCCTTGTCTTATGTCCAGAATGC-3' | generate a PCR product that is denatured well below 94° C. Typical denaturation temperatures for PCR are 94°–96° C. At the lowered temperature the double-stranded DNA (i.e., the expected "contaminant") is not denatured and would not be amplified. Methods for affecting the denaturation temperature of PCR products are described in detail in copending U.S. Ser. No. 718,576, filed Jun. 20, 1991, and incorporated herein by reference.

Alternatively, unconventional nucleotides are useful for effecting the denaturation temperature of the PCR product. For example, hydroxymethyl dUTP (HmdUTP) naturally occurs in SP01 phage DNA as 5' hydroxymethyluracil (HmUra) in place of thymine (Kallen et al., 1962, *J. Mol. Biol.* 5: 248–250, and Levy and Teebor, 1991, *Nuc. Acids Res.* 19(12):3337, which are both incorporated herein by reference). The HmUra containing genome melts at 10° C. less than DNA of corresponding thymine content. Incorporation of HmdUMP into cDNA effectively lowers the denaturation temperature of both the reverse transcribed product and the PCR duplex DNA product, in comparison to the denaturation temperature of the homologous thymine containing DNA. Other modified nucleoside triphosphates capable of effecting the Tm of the DNA product (e.g., $c^7$dGTP, 7 deaza-2'deoxyguanosine 5'-triphosphate or α-phosphorothioate dNTPs) are also suitable for distinguishing between homologous RNA and DNA templates.

Following removal or melting of the RNA template strand, the remaining cDNA strand can then serve as a template for polymerization of a self-complementary strand, providing a double-stranded cDNA molecule suitable for additional amplification, detection or other manipulation. The second strand synthesis also requires a primer. A sequence specific primer can be introduced into the reaction mix to prime second strand synthesis. Alternatively, a duplex adapter-linker may be ligated to the cDNA or the cDNA may be tailed with a terminal transferase-type activity. The second strand primer needs only to hybridize to the tail rather than the specific cDNA sequence (see for example, Frohman in Innis et al., supra.). In the practice of the disclosed methods, it may be desirable to use a first set of primers to synthesize a specific cDNA molecule and a second nested set of primers to amplify a desired cDNA segment. All of these reactions may be catalyzed by the same thermostable DNA polymerase.

For reverse transcription, according to the present invention, the primer-template mixture is incubated with a thermoactive or thermostable polymerase under suitable polymerization conditions. These conditions are provided by a reaction mixture containing all four deoxyribonucleotide triphosphates (dNTPs) and a buffer containing a buffering agent, a divalent cation, and a monovalent cation.

DNA polymerases require a divalent cation for catalytic activity. Tabor and Richardson, 1989, *Proc. Natl. Acad. Sci. USA* 86:4076–4080, incorporated herein by reference, have reported that $Mn^{+2}$ can be substituted for $Mg^{+2}$ in DNA sequencing methods. These methods require a DNA template and T7 DNA polymerase or DNA polymerase I.

Either $Mn^{+2}$, $Mg^{+2}$, or $Co^{+2}$ can activate Taq, Tth, and Tma DNA polymerases; however, $Mn^{+2}$ is preferred in the present methods. In the disclosed embodiments of the invention, buffers are provided which contain $Mn^{+2}$ for nucleic acid reverse transcription from an RNA template. These buffers are improved over previous reverse transcription buffers and result in increased cDNA yields. In particular, practice of the present methods using Tth DNA polymerase and $MnCl_2$ or $Mn(OAc)_2$ for amplifying RNA imparts an increase in sensitivity of at least $10^6$-fold compared to $MgCl_2$ and standard PCR conditions. While capable of activating RNA template-directed DNA synthesis, mixed divalent cation buffers (e.g., $Mn^{+2}$ and Mg+2), are not preferred due to reduced sensitivity and efficiency.

The divalent cation is supplied in the form of a salt such $MgCl_2$, $Mg(OAc)_2$, $MgSO_4$, $MnCl_2$, $Mn(OAc)_2$, or $MnSO_4$. Usable cation concentrations in a Tris-HCl buffer are for $MnCl_2$ from 0.5 to 7 mM, preferably, between 0.5 and 2 mM, and for $MgCl_2$ from 0.5 to 10 mM. Usable cation concentrations in a Bicine/KOAc buffer are from 1 to 20 mM for $Mn(OAc)_2$, preferably between 2 and 5 mM.

Preferably, the monovalent cation is supplied by the potassium, sodium, ammonium, or lithium salts of either chloride or acetate. For KCl, the concentration is between 1 and 200 mM, preferably the concentration is between 40 and 100 mM, although the optimum concentration may vary depending on the polymerase used in the reaction. Optimal reverse transcriptase activity is observed between 50 and 75 mM KCl when Tth DNA polymerase is used. However, enhanced RT/PCR is observed when the KCl concentration is increased up to 100 mM. For AmpliTaq® DNA polymerase, 50 mM KCl is preferred. For KOAc, optimal reverse transcriptase activity is observed at concentrations between 85 mM and 115 mM when Tth DNA polymerase is used.

Deoxyribonucleotide triphosphates are added as solutions of the salts of dATP, dCTP, dGTP, dUTP, and dTTP, such as disodium or lithium salts. In the present methods, a final concentration in the range of 1 μM to 2 mM each is suitable, and 100–600 μM is preferable, although the optimal concentration of the nucleotides may vary in the reverse transcription reaction depending on the total dNTP and divalent metal ion concentration, and on the buffer, salts, particular primers, and template. For longer products, i.e., greater than 1500 bp, 500 μM each dNTP and 2 mM $MnCl_2$ may be preferred when using a Tris-HCl buffer.

A suitable buffering agent is Tris-HCl, preferably pH 8.3, although the pH may be in the range 8.0–8.8. The Tris-HCl concentration is from 5–250 mM, although 10–100 mM is most preferred. A preferred buffering agent is Bicine-KOH, preferably pH 8.3, although pH may be in the range 7.8–8.7. Bicine acts both as a pH buffer and as a metal buffer.

Additionally, EDTA less than 0.5 mM may be present in the reverse transcription reaction mix. Detergents such as Tween-20™ and Nonidet™ P-40 are present in the enzyme dilution buffers. A final concentration of non-ionic detergent approximately 0.1% or less is appropriate, however, 0.01–0.05% is preferred and will not interfere with polymerase activity. Similarly, glycerol is often present in enzyme preparations and is generally diluted to a concentration of 1–20% in the reaction mix. A mineral oil overlay may be added to prevent evaporation but is not necessary when using a TC9600 thermal cycler (Perkin Elmer, Norwalk, Conn.) or when using Ampliwax™ PCR Gem 100 (Perkin Elmer, Norwalk, Conn.) as described in PCT Patent Publication No. WO 91/12342 and Chou et al., 1992, *Nuc. Acids. Res.* 20:1717–1723, which are incorporated herein by reference.

In one embodiment of the invention, a method for homogeneous RT/PCR is provided. This two-step, single addition procedure eliminates the need to open the tube after the addition of initial reagents. Thus, the opportunity for contamination between the RT and PCR steps is removed. However, the opportunity to change reaction reagents between steps is also eliminated and the two reactions need to be performed under the same reaction reagent conditions, which may not be optimal for both the RT and PCR steps. Adjustment of reaction conditions may be required to accommodate the separate requirements of the two reaction steps. For example, due to the high enzyme concentration required for optimum RT activity, a short extension cycle is preferred, i.e., 10–30 seconds, during each PCR thermal Cycler when amplifying short targets, although the extension cycle time may depend on the thermal cycler used. For example 1 minute is preferred when using a TC480 thermal cycler marketed by Perkin Elmer, Norwalk, Conn.

Similarly, because there is no buffer adjustment between the RT and PCR steps in a homogeneous RT/PCR assay, a manganese concentration intermediate to the separate RT and PCR optima is required such that each step functions. As shown in Example XIV, the optimal concentration is lower for the DNA target, PCR reaction than it is for the RNA target, RT reaction. The manganese concentration providing optimal synthesis on DNA templates was found to be approximately 0.6 mM (with 800 μM total dNTP, Tris buffer), the enzyme obtained maximal reverse transcriptase activity on the RNA template at approximately 1.4 mM manganese (with 800 μM total dNTP, Tris buffer). For the homogeneous reaction described in Example X, the MnCl$_2$ concentration is preferably equal to or less than 1.0 mM and, most preferably, 0.8 mM. While the preferred concentrations represent conditions which allow Tth DNA polymerase to perform RT/PCR, these conditions are suboptimal for both reverse transcription and DNA amplification. Furthermore, although the efficiency of the RT step in the presence of dUTP, as in the sterilization methods of the present invention, is improved at higher MnCl$_2$ concentration, the PCR step is less efficient. Consequently, 0.8 mM MnCl$_2$ most preferably is used and the product is detected by means more sensitive than ethidium stained gels; i.e., probe hybridization or incorporation of labeled, or other detectable nucleotides.

One method of solving the problem of different optimal reaction conditions for the two steps involves the use of a high melting temperature wax (72° C.) in the reaction tube to separate reagents as described in PCT Patent Publication No. WO 91/12342. The high melting temperature wax essentially enables the two individual reactions to occur at their own optimal conditions by separating a solution of EGTA and MgCl$_2$ from the RT reaction with a wax layer. The RT step is carried out at a temperature below the melting point of the wax, hence, the wax layer remains intact and the RT step is carried out using manganese at an optimal concentration. Upon completion of the RT step, the wax is melted during the first high temperature denaturation step of the PCR, thus releasing the EGTA to preferentially chelate the manganese and allow for a magnesium based DNA amplification. A modification of this technique employs microencapsulating the EGTA and magnesium into a bead made of the same high melting temperature wax.

A metal buffer whose buffering agent acts as a chelating agent that binds manganese allows a higher Mn$^{+2}$ concentration to be used. The metal buffer may maintain the available Mn$^{+2}$ concentration at a constant level over a wide range of added Mn$^{+2}$. Metal buffering agents which can be useful in the methods of the present invention include N,N-Bis(hydroxyethyl)glycine (bicine), N-Tris (hydroxymethyl)methylglycine (tricine), acetate, glutamate, aspartate, N-hydroxyethyliminodiacetic acid (HIMDA), citrate, and isocitrate. A combination of buffering agents which provides similar metal binding and pH buffering capabilities as one of the exemplified buffers may also be suitable. The term "buffering agent," as used herein, is meant to encompass such combinations of buffering agents. In some cases, similar buffering effects may be achieved by altering the concentration of the buffering agent. For example, Example XX describes the use of an elevated Tris concentration to achieve a broadening of the manganese range.

The metal buffering agent, which acts as a chelating agent, forms complexes with the metal cation in a reversible reaction. The stability of the chelator-metal complex, which represents the affinity of the chelator for the metal cation, is expressed as a "metal-buffer binding constant" or "stability constant", $K_M$. Because of the wide range of stability constants, it is more common to refer to the logarithm (base 10, written herein as Log) of the $K_M$ of a metal buffer. The stability constant, $K_M$, is described in Good et al., 1966, *Biochemistry* 5:467–477, and Perrin and Dempsey, 1974, Chapter 7 in *Buffers for pH and Metal Ion Control*, Chapman and Hall, New York, N.Y., which are incorporated herein by reference. Suitable metal buffers that bind manganese for use in the methods of the present invention have a Log $K_M$ (20° C., 0.1M ionic strength) between 1 and 6 (i.e., $10 < K_M < 10^6$). Preferably the Log $K_M$ is between 2 and 4, and most preferably between 2.5 and 3.5. A compilation of stability constants for a variety of chelating agents is provided in Martell and Smith, 1974, *Critical Stability Constants*, Plenum Press, New York, N.Y., Vol 1; Martell and Smith, 1977, *Critical Stability Constants*, Vol 3, Plenum Press, New York, pages 160–162; and Sillen and Martell, 1964, *Stability Constants of Metal-Ions Complexes*, Spec. Publ. Chem. Soc. n17, page 458, London, which are incorporated herein by reference.

Preferred metal buffers are also capable of serving as hydrogen ion buffers in the pH range required in the methods of the present invention. Good et al., supra, described a class of buffers that serve both as metal cation and hydrogen ion buffers. The acid dissociation constant of a buffer, $K_a$, is described in Good et al., 1966, supra, and Perrin and Dempsey, 1974, supra. It is preferred that the buffer have a p$K_a$, defined as −Log $K_a$, between 7 and 9 at 20° C. and 0.1M ionic strength, preferably between 7.5 and 8.5.

Preferred buffering agents for use in the methods of the present invention include N,N-Bis(hydroxyethyl)glycine (bicine) and Tris(hydroxymethyl)methylglycine (tricine). Both of these are zwitterionic aliphatic amines; more specifically, substituted glycines with carboxyl groups providing the Mn$^{+2}$ binding ability. A comparison of properties of bicine, tricine, and Tris(hydroxymethyl)aminomethane (Tris) are shown below and found in Good et al., 1966, supra., which additionally provides the structures. All values are at 20° C. and 0.1M ionic strength.

| Buffer | pK$_a$ | delta-pK$_a$/°C. | Log K$_M$ (Mn$^{+2}$) |
| --- | --- | --- | --- |
| Tris | 8.3 | −0.031 | negligible |
| Bicine | 8.35 | −0.018 | 3.1 |
| Tricine | 8.15 | −0.021 | 2.7 |

The changes in the acid binding constant with temperature (delta-pK$_a$) for bicine and tricine are significantly lower than for Tris-HCl. Tricine and Bicine also reduce the large temperature dependence of pH found with Tris.

Tricine and bicine buffers also broaden the usable Mn$^{+2}$ concentration range in DNA polymerase incorporation assays. As the concentration of tricine or bicine is increased, the decrease in DNA polymerase activity at increasing Mn$^{+2}$ concentration is less pronounced and the Mn$^{+2}$ concentration optimum is shifted to a higher concentration. As shown in Example XIV, using Tth DNA polymerase in a 50 mM bicine-KOH buffer (pH 8.3), manganese concentrations of 0.4 mM to 2.6 mM gave good incorporation on a DNA template. Using an RNA template, approximately 40% of maximum activity was observed with a Mn$^{+2}$ concentration as low as 1 mM. Activity was observed to increase as the manganese concentration was increased from 1.0 to 6 mM and reached a plateau for concentrations between approximately 6 and 12.5 mM. A gradual decrease of activity was observed at higher Mn$^{+2}$ concentrations; 48% of maximum activity was observed at 20 mM.

In the combined RT/PCR, a low free manganese ion concentration is needed for the DNA amplification step, but a high free manganese ion concentration is needed for the reverse transcription step. This dual effect of the tricine and bicine buffers of the present invention, that of extending the total allowed manganese concentration in a DNA amplification by complexing most of the free manganese ion, yet providing sufficient free manganese for the RT reaction, provides significant improvements to the RT/PCR. This is a very surprising result because expansion of the dual ranges would not have been predicted given the general theory and literature behind metal buffers.

Since reaction components such as dNTPs, primers, nucleic acids, proteins, EDTA, and many materials carried over from sample preparation procedures have the ability to chelate manganese, the control of a precise concentration of manganese is very difficult. Although these components can be controlled by the individual researcher (with great care), severe constraints are placed on manufacturing these reagents for diagnostic and research applications on a large scale. The use of the metal buffers tricine and bicine not only shifts the optimal $Mn^{+2}$ concentration upwards, but also broadens the usable range of $Mn^{+2}$ concentration and dNTP concentration. The ability to use a higher manganese concentration and a broader range of concentrations eases the problems of reagent manufacture and of precisely controlling the manganese concentration in a reaction.

Although the metal binding constant (Log $K_M$) of Tris is thought to be negligible (Good et al., 1966, supra), increasing the concentration of Tris-HCl in an RT/PCR from 10 mM to 100 mM can expand the $Mn^{+2}$ concentration range on RNA targets. Although Tris buffer was thought to bind $Mn^{+2}$ (as well as most other metals) negligibly, Morrison, 1979, Methods Enzymol. 24b:53–68, indicates that "the dissociation constant for the Mn-Tris complex is high at 250 mM, but in a solution of 100 mM Tris and 2 mM $Mn^{+2}$ almost 29% of the metal ion would be chelated." Example XX describes the use of 100 mM Tris in an RT/PCR which provided a significant broadening of the manganese concentration range wherein amplified product was observed. The amount of broadening was surprising and would not have been predicted given the general theory and literature behind metal buffers and Tris, in particular.

Bicine and tricine buffers preferably contain either KCl or KOAc as the monovalent cation. The bicine/KOAc buffer has a slightly lower ionic strength than the bicine/KCl buffer which could help destabilize secondary structures in a template with a high G+C content. The pH of the KOAc added to the reaction is not too critical because the bicine, which acts both as a metal buffer and a pH buffer, buffers the pH of the reaction adequately. Product was observed using KOAc between pH 7.0 and 9.4, with the optimum being pH 7.5. The final pH of a solution of 50 mM bicine (pH 8.3), 100 mM KOAc (pH 7.5), and 2.5 mM $Mn(OAc)_2$ is 7.97.

The bicine buffer solutions can be stored for extended lengths of time. For example, the product formed in an RT/PCR using a buffer diluted from a 10× solution of 500 mM bicine, 800 mM KCl, and 21 mM $MgCl_2$ stored at 4° C. for 47 days was equal to the product formed in an RT/PCR using a freshly made buffer. The bicine maintains solubility of metal ions; an additional advantage of using the preferred bicine/KOAc/$Mn(OAc)_2$ buffer for RT/PCR is that $Mn(OAc)_2$ will have fewer solubility problems as compared to $MnCl_2$. Therefore, precipitation of manganese hydroxides and oxides, which are detrimental in RT/PCR, can be prevented.

The sterilization methods of the present invention specify that the RT/PCR be performed in the presence of dUTP. Maximum efficiency of uracil N-glycosylase (UNG) sterilization is achieved when dUMP is incorporated in place of every dTMP in the contaminating template. To maximize dUMP incorporation, it is desirable to minimize the amount of dTTP added to the RT/PCR because Tth DNA polymerase discriminates against dUTP when dTTP is present during reverse transcription by approximately 2-fold. Because dNTP binds $Mn^{+2}$, the free $Mn^{+2}$ concentration is directly related to the dNTP concentration. The bicine/KOAc buffer that increases the usable $Mn^{+2}$ concentration range also allows an increased concentration of dNTP to be used at a given $Mn^{+2}$ concentration because the buffering of the free $Mn^{+2}$ concentration compensates for the additional $Mn^{+2}$ binding by the dNTP. The bicine/KOAc buffer not only allows increased total dNTP concentrations, but also allows higher relative concentrations of dUTP to be used during the RT/PCR to increase the levels of incorporation of dUMP during the reverse transcription step by rTth DNA polymerase. This is particularly advantageous in RNA targets that have a large percentage of adenine residues, such as human immunodeficiency virus (HIV).

A further advantage of the preferred bicine and trichinae buffers of the present invention is that they increase the efficiency of the sterilization methods. Both divalent metal cations and high ionic strength are known to inhibit UNG (Lindahl et al., 1977, J. Biol. Chem. 252(10):3286–3294, Krokan and Witter, 1981, Nucl. Acids Res. 9(11):2599–2613, and Caradonna and Cheng, 1980, J. Biol. Chem. 255(6):2293–2300, which are incorporated herein by reference). The preferred buffers reduce both the free metal cation level and the total ionic strength, thereby minimizing the inhibitory effect of the buffer on UNG and improving the efficiency of the sterilization of the reaction mixture.

Metal ion catalyzed hydrolysis of the RNA template decreases the efficiency of the RT reaction and limits the length of template that can be reverse transcribed. The problem of template hydrolysis is aggravated by the high temperature of the RT step in the present methods. Methods and reaction conditions using $MnCl_2$ in a Tris buffer which minimize the hydrolysis of RNA templates are provided in the Examples and discussed in Myers and Gelfand, 1991, Biochemistry 30:7661–7666, which is incorporated herein by reference. The preferred bicine/KOAc buffers complex the manganese such that less metal catalyzed RNA hydrolysis occurs at elevated temperatures. Furthermore, little if any additional loss of full-length labeled RNA occurs by including a 15 second, 95° C. preincubation of the RNA when using these buffers. The preferred buffers allow increasing the reverse transcription reaction time to increase efficiency in the RT step and including a high temperature preincubation to denature the RNA to relieve high degrees of secondary structure prior to reverse transcription or, in the case that double-stranded RNA template is to be amplified, to denature the template to provide a single-stranded template for the reverse transcription. Furthermore, decreasing RNA hydrolysis facilitates the synthesis of long (>2 kb) cDNA using Tth DNA polymerase by decreasing the chance that the RNA template is degraded before reverse transcription is completed.

The present methods require only that RNA is present in the sample. In an example, a synthetic RNA prepared using a plasmid containing a bacteriophage T7 promoter is reverse transcribed and amplified by the methods of the present invention. In another example, a heterogeneous population of total cellular RNA is used to reverse transcribe and amplify a specific mRNA. For practicing the invention the amount of RNA present in the sample is generally within the range of 0.1 pg to 1 µg. The amount required and the results will vary depending on the complexity of the sample RNA and the type of detection utilized. Because of the specificity of the high temperature reverse transcription reaction, 1 to $10^8$ molecules of the target RNA are sufficient to provide up to or exceeding microgram quantities of PCR product. In several of the disclosed examples, amplification products are visualized by ethidium bromide staining after gel electrophoresis of 5% of the total reaction mix. Thus, the amount of amplified target required is substantially reduced when alternative means for assay of the product are utilized. For example, isotopically labeled DNA probes suitable for detecting the electrophoresed PCR products would increase the sensitivity of detection and therefore decrease the amount of amplification or number of cycles required to detect the amplified product (e.g., $1-10^8$ molecules of target RNA in the sample).

Preferably, the amount of RNA present in a 20 µl 10 mM Tris-HCl reverse transcription reaction is 10 pg to 500 ng and most preferably 0.1 to 300 ng. When the sample contains more than 300 ng of RNA, it may be desirable to include additional enzyme to ensure transcription of a full length cDNA product from the RNA template. However, if the reverse transcription reaction is coupled to PCR, the effect of high enzyme concentration in the PCR reaction should be considered. For example when Taq DNA polymerase is used as the thermoactive polymerase, high enzyme concentrations can result in non-specific PCR products and reduced yields (see Saiki in *PCR Tech. Ed.* Erlich, 1989, Stockton Press, incorporated herein by reference). The potential problems resulting from a high enzyme concentration, however, are easily avoided by inactivating the thermoactive DNA polymerase between the reverse transcription reaction and the amplification reaction. Inactivation is achieved by incubating the cDNA synthesis reaction mix at 99° C. for 3 to 10 minutes. An appropriate amount of thermostable DNA polymerase is then added back to the reaction mix, and PCR is conducted as usual. This method is also suitable when different thermostable DNA polymerases are used for each of the two reactions, as exemplified in Example VII.

An advantage of the bicine buffers described herein is that higher amounts of RNA may be present in the reverse transcription reaction. For example, the preferred amount of RNA using a bicine buffer and dTTP is up to 1 µg for a 50 µl reaction. In the preferred range, 1 to 10 units of thermoactive DNA polymerase is sufficient for providing a full length cDNA product. To achieve predominantly full length cDNA, the enzyme to template ratio is preferably greater than 0.5.

An advantage of the RT/PCR methods using Tth or Taq DNA polymerase is that lower molar concentrations of the DNA polymerase are needed for efficient reverse transcription and amplification. For example, each unit of activity requires about 1.0 pmole of *E. coli* DNA polymerase I, whereas only about 0.043 pmole of Taq DNA polymerase is required, or about 20- to 25-fold less protein. Example X describes a homogeneous RT/PCR which uses 5 units of rTth DNA polymerase in a 20 µl reaction, corresponding to approximately a 15 nM DNA polymerase concentration. Using the preferred bicine and tricine buffers, the amount of DNA polymerase can be reduced further. Examples XV, XVII, and XIX describe homogeneous RT/PCR using 10 units rTth DNA polymerase in 100 µl reactions, corresponding to approximately a 6 nM DNA polymerase concentration. Furthermore, the one enzyme RT/PCR described herein requires considerably less total protein in the reaction compared to multi-enzyme amplification systems such as 3SR (Kwoh et al., supra., Guatelli et al., supra., and PCT Patent Publication No. WO 92/0880A). Whereas the exemplified 100 µl RT/PCR reactions contain 40 ng (10 units) of rTth DNA polymerase, a 100 µl 3SR reaction would contain 1.44 µg of enzyme (0.6 µg AMV-RT, 0.83 µg T7 RNA polymerase, and 0.01 µg *E. coli* RNase H) or about 36 times more protein. Both the decrease in total protein and the use of only one enzyme in the homogeneous RT/PCR significantly simplify problems of reagent manufacture and quality control.

Once the sample containing RNA has been prepared and the suitable primer and salts have been added, the reaction is incubated with the thermoactive DNA polymerase for 1–60 minutes. Usually, however, a reaction time of 2 to 30 minutes is suitable. If the target molecule is long, or if the ratio of total RNA to target RNA is high, e.g., 100 copies of target RNA in the presence of 250 ng of total RNA, an incubation time of 10–30 minutes is preferred.

It is preferred, but not essential that the thermoactive DNA polymerase is added to the reverse transcription reaction mix after both the primer and the RNA template are added. Alternatively, for example, the enzyme and primer are added last, or the $MnCl_2$, or template plus $MnCl_2$ are added last. It is generally desirable that at least one component that is essential for polymerization activity not be present, until such time as the primer and template are both present and the enzyme can bind to and extend the desired primer/template substrate (see U.S. patent application Ser. No. 07/890,300, filed May 27, 1992, which is incorporated herein by reference).

In practicing the present methods the reaction mix is incubated above 40° C., although a preferred temperature is 55°–75° C. At this temperature, the specificity of the primer-template annealing is enhanced over the annealing specificity at a lower temperature, and the thermoactive enzyme has higher activity at the elevated temperature. The elevated temperature reduces non-specific priming by degraded native nucleic acid and by incorrect primer-template hybridization.

Following reverse transcription, the RNA template may be degraded or alternatively denatured, providing a template for continuous replication resulting in an excess of single-stranded DNA molecules. This excess of single-stranded DNA can be detected by standard probe hybridization techniques. Thus, the invention provides means for direct detection of target segments. The resulting nucleic acid products can be detected by a number of electrophoretic or chromatographic means. The use of a radiolabeled triphosphate is helpful in monitoring the extent of the reaction and the size of products formed, although this is not an essential component of the invention.

The reverse transcription reaction products am suitable as templates for amplification by PCR. In one embodiment of the invention, following the high temperature reverse transcription incubation, the reverse transcription reaction is adjusted to PCR buffering conditions, and the amplification reaction is initiated following the addition of a second primer. PCR buffer is added to maintain the appropriate buffering capacity, pH, monovalent cation concentration, and to dilute the concentration of enzyme and dNTPs to within 20–200 µM each dNTP. $MgCl_2$ is added to a final concentration of 1–3 mM. Preferably, the concentrations of dNTPs in both the reverse transcriptase and PCR reaction mixes are balanced. Because $Mn^{+2}$ can diminish PCR amplification when present at high concentrations, in a preferred embodiment of the invention the $Mn^{+2}$ is chelated prior to the PCR amplification. The presence of high amounts of $Mn^{+2}$ also may decrease fidelity during amplification, however chelating the $Mn^{+2}$ avoids this problem. Accordingly, in a preferred embodiment, following the reverse transcription reaction, EGTA is added to a concentration between about 1–3 times the molar concentration of $Mn^{+2}$ to chelate the $Mn^{+2}$. In the presence of both $Mg^{+2}$ and $Mn^{+2}$, EGTA preferentially binds $Mn^{+2}$. Low dNTP and $Mg^{+2}$ concentrations, as described herein, may also increase fidelity of Tth DNA polymerase during amplification. Glycerol and non-ionic detergent (for example, Tween-20™) may be added to a final concentration of between 1–20% and 0.01–0.05%, respectively, to increase enzyme stability.

In an alternative preferred embodiment, $Mn^{+2}$ is not chelated prior to PCR. PCR can utilize $Mn^{+2}$ in place of Mg+2, although $Mg^{+2}$ is preferred as described above. In particular, for applications such as, for example, large scale diagnostic screening, the risk of infidelity during amplification and potential low level hydrolysis of template are readily tolerated in view of the tremendous advantages a homogeneous RT/PCR method provides. The two-step single addition procedure minimizes sample handling and reduces the potential for cross contamination. Because $MnCl_2$ affects PCR efficiency, the optimum concentration is preferably titrated by standard means for the particular reaction components utilized: primers, target concentration, dNTP concentration, buffers, salts etc. In a preferred embodiment of the invention, a bicine/KOAc buffer containing $Mn(OAc)_2$ is used which allows for a wider range of $Mn^{+2}$ and dNTP concentrations.

The methods provided herein have numerous applications, particularly in the fields of molecular biology and medical diagnostics. The reverse transcriptase activity described provides a cDNA transcript from an RNA template. The methods for production and amplification of DNA segments from an RNA molecule are suitable where the RNA molecule is a member of a population of total RNA or is present in a small amount in a biological sample. Detection of a specific RNA molecule present in a sample is greatly facilitated by a thermoactive or thermostable DNA polymerase used in the methods described herein. The enormous increase in specificity obviates the need for "nested PCR" to detect rare targets. A specific RNA molecule or a total population of RNA molecules can be amplified, quantitated, isolated, and, if desired, cloned and sequenced using a thermoactive or thermostable enzyme as described herein.

The methods and compositions of the present invention are a vast improvement over prior methods of reverse transcribing RNA into a DNA product. When starting with an RNA template, these methods have enhanced specificity and provide templates for PCR amplification that are produced more efficiently than by previously available methods. The invention provides more specific and, therefore, more accurate means for detection and characterization of specific ribonucleic acid sequences, such as those associated with infectious diseases, genetic disorders, or cellular disorders.

Those skilled in the art will recognize that the compositions of the instant invention can be incorporated into kits. Thus, the invention relates to kits that contain a thermoactive DNA polymerase as well as instructions describing the method for using the same for reverse transcribing RNA. In one embodiment such a kit may relate to the detection of at least one specific target RNA sequence in a sample. Such a kit would comprise, in addition to the elements listed above, a primer comprising a sequence sufficiently complimentary to a specific target RNA sequence to hybridize therewith. Diagnostic kits for the amplification and detection of at least one specific RNA sequence in a sample may comprise a primer having a sequence sufficiently identical with the RNA target to hybridize with the first strand of cDNA synthesized to prime synthesis of a second cDNA strand. Kits may contain, in addition to the components listed, the four deoxyribonucleotide triphosphates, suitable buffers as described herein, oligo(dT), RNase H, linkers for cloning, as well as one or more restriction enzymes.

The following examples are offered by way of illustration only and should not be construed as intending to limit the invention in any manner.

Example I

Materials and Methods

I. Substrates

A. RNA

RNA was synthesized in vitro using T7 RNA polymerase and a synthetic template, pAW106. The template, pAW106, contains a T7 promoter adjacent to a synthetically prepared DNA segment followed by a polyadenylation sequence. The RNA produced, referred to herein as cRNA, was purified by oligo(dT) chromatography. The purified material, 1060 bases in length, contained a portion of interleukin 1 (IL-1 β) mRNA sequence. The RNA concentration was 0.1 μg/μl which was equivalent to ~0.286 pmoles/μl.

Alternatively, pAW109 (ATCC No. 68152) was used as a template to prepare cRNA, 963 bases in length. Whether pAW106 or pAW109 cRNA was used, the cRNA was prepared and quantitated according to Wang et al. supra. In some examples pAW109 cRNA was diluted to limit the number of template molecules and *E. coli* ribosomal RNA (Boehringer Mannheim, Indianapolis, Ind.) was added for a total of 60 ng of RNA/reaction.

K562, a Philadelphia-chromosome positive cell line (Lozzio and Lozzio, 1975, *Blood* 45:321–334, and Kawasaki et al., 1988, *Proc. Natl. Acad. Sci. USA* 85:5698–5702, both incorporated herein by reference), was used as a source of total cellular RNA. The RNA was purified according to Kawasaki et al., 1985, *Science* 235:85–88, and Schwartz et al., 1981, *J. Immunol.* 126:2104–2108, both incorporated herein by reference.

B. DNA

A DNA template was provided as a control for monitoring the activity of DNA polymerase. A solution of activated salmon sperm DNA was prepared at a concentration of 2.5 μg/μl in 10 mM Tris-HCl, pH 8.3, 5 mM KCl, and 50 μM EDTA. One reaction contained 6.25 μg of salmon sperm DNA template (2.5 μl). In some examples pAW109 was diluted to limit the number of template molecules and *E. coli* ribosomal RNA (Boehringer Mannheim, Indianapolis, Ind.) was added for a total of 60 ng of RNA/reaction.

II. Oligonucleotide Primers

DM156 (SEQ ID No. 9) was used to prime cDNA synthesis using the pAW106 cRNA template. The primer sequence corresponds to a portion of the human IL-1 β gene and is complementary to human IL-1β mRNA. The primer concentration was 100 pmol/μl.

DM152 (SEQ ID No. 11) and DM151 (SEQ ID No. 10) correspond to a portion of the human IL-1α gene and amplify a 420 bp segment when IL-1 α mRNA (for example, from K562 cells) is used as the template. A 308 bp segment is produced from pAW109 cRNA. DM152 (SEQ ID No. 11) hybridizes to pAW109 cRNA or IL-1α mRNA to prime cDNA synthesis. DM151 (SEQ ID No. 10) hybridizes to the single-stranded cDNA as the "upstream" amplification primer.

TM01 (SEQ ID No. 12) was used as the "downstream" primer to synthesize a cDNA molecule from the pAW109 cRNA template and can hybridize to the 3' untranslated region of human IL-1 α mRNA. DM 151 (SEQ ID No. 10) and TM01 (SEQ ID No. 12) amplify a 736 bp segment of pAW109.

| | | |
|---|---|---|
| DM156 | SEQ ID No. 9 | 5'-TGGAGAACACCACTTGTTGCTCCA-3' |
| DM151 | SEQ ID No. 10 | 5'-GTCTCTGAATCAGAAATCCTTCTATC-3' |
| DM152 | SEQ ID No. 11 | 5'-CATGTCAAATTTCACTGCTTCATCC-3' |
| TM01 | SEQ ID No. 12 | 5'-GCTTGCAAGCTTTATTTAGTTATGACTGATAACACTC-3' |

III. Deoxyribonucleoside Triphosphates

The amount of reverse transcription (RT) product formed was monitored by the incorporation of [α-$^{32}$P]dCMP. Therefore, a dNTP minus C stock was prepared comprising 2 mM dATP, 2 mM dTTP, and 2 mM dGTP. A 330 μl, 1 mM dCTP solution was prepared containing 100 μCi [α-$^{32}$P] dCTP (New England Nuclear, Boston, Mass.). Therefore, approximately $6.6 \times 10^5$ dpm represents $10^3$ pmoles dCMP incorporated. The dNTP minus C and dCTP solutions were combined to prepare a 5× dNTP stock mix containing 1 mM dATP, 1 mM dTTP, 1 mM dGTP, and 250 μM [α-$^{32}$P]dCTP. Alternatively, when no radio-labeled triphosphate is used, all four dNTPs are included in the reverse transcription reaction at 200 μM. For convenience a solution containing 2 mM each of dATP, dCTP, dGTP and dTTP in H$_2$O, pH 7.0, is prepared as a 10× stock solution. Alternatively, reverse transcription/PCR product was monitored by agarose gel electrophoresis and ethidium bromide staining.

IV. Buffers

A. Annealing Buffer

The 10× stock annealing buffer was prepared containing 100 mM Tris-HCl pH 8.3, 500 mM KCl and 1 mM EDTA.

B. Modified Pol I 10× Buffer

The 10× Pol I buffers were prepared with and without MgCl2 containing 100 mM Tris-HCl, pH 8.3, 500 mM KCl, 10 mM DTT, and 60 mM MgCl$_2$ if present.

C. Taq DNA Polymerase/Reverse Transcription 10× Buffer (HSB) The 10× Taq buffer was prepared containing 100 mM Tris-HCl, pH 8.3 and 500 mM KCl.

D. 10X Low Salt Buffer (LSB)

The 10× LSB was prepared containing 100 mM Tris-HCl, pH 8.3 and 50 mM KCl.

E. 10× RT Reaction Buffer

The 10× RT buffer was prepared containing 100 mM Tris-HCl (pH 8.3) and 900 mM KCl.

F. MoMuLV-RT 10× Buffer

The 10× MoMuLV-RT buffer was prepared as in C, above, with the addition of 60 mM MgCl$_2$.

G. 10× PCR Buffer

The 10× PCR buffer was prepared containing 100 mM Tris-HCl, pH 8.3, 1 M KCl, 18.75 mM MgCl$_2$, 7.5 mM EGTA, and 50% glycerol (v/v).

H. 10× Taq PCR Buffer

The 10×Taq PCR buffer contained 100 mM Tris-HCl (pH 8.3), 300 mM KCl, and 25 mM MgCl$_2$.

I. Taq Diluent

Taq dilution buffer was prepared comprising: 25 mM Tris-HCl, (pH. 8.8), 100 mM KCl, 0.1 mM EDTA, 0.5% Tween-20™, 0.5% Nonidet™ P-40, and 500 μg/ml gelatin.

V. Enzymes

A. Reverse Transcriptase (MoMuLV-RT) was obtained from Bethesda Research Labs, Bethesda, Maryland at a concentration of 200 U/μl. The enzyme was diluted in Taq Diluent with 1/5 concentration of Tween-20™ and Nonidet™ P-40 to provide 4, 0.4, 0.04, and 0.004 U/μl preparations.

B. E. coli Pol I was purchased from New England Biolabs, Beverly, Mass., at a concentration of 10 U/μl.

C. Native Taq (94 kDa), developed and manufactured by Hoffmann-La Roche Inc. and commercially available from Perkin Elmer, Norwalk, Conn., was provided at a concentration of 48 units/μl. The specific activity was approximately 240,000 units/mg. Taq diluent was used to reduce the concentration to 10 U/μl.

D. rTaq DNA Polymerase, Stoffel Fragment

The Stoffel fragment of Taq DNA polymerase is a truncated form of 94 kDa Taq in which the amino terminal 289 amino acids have been deleted. Although the enzyme is 61 kDa in size, it has previously been referred to as 62 kDa Taq. The enzyme can be produced in and purified from recombinant host cells as described in U.S. Pat. No. 5,079,352 and Lawyer et al., 1993, supra. Stoffel fragment was developed and manufactured by Hoffmann-La Roche Inc. and is commercially available from Perkin Elmer, Norwalk, Conn., as AmpliTaq® DNA polymerase, Stoffel Fragment.

E. Tth Polymerase

Native Tth polymerase is commercially available from Pharmacia, Piscataway, NJ, and Boehringer Mannheim, Indianapolis, Ind. Methods for purifying 94 kDa native Tth DNA polymerase and producing and purifying recombinant 94 kDa Tth DNA polymerase are described in PCT Patent Publication No. WO 91/09950. For use in the present examples, recombinant Tth (rTth) DNA polymerase purified as described below, was developed and manufactured by Hoffmann-La Roche Inc. and is commercially available from Perkin Elmer, Norwalk, Conn.

rTth DNA polymerase was purified from E. coli strain DG 116 containing plasmid pLSG33. As described at page 46 of the specification of PCT Patent Publication No. WO 91/09950, pLSG33 was prepared by ligating the Tth DNA polymerase encoding NdeI-BglII restriction fragment of pLSG24 into NdeI-BamHI digested expression vector pDG178. The resulting plasmid is ampicillin resistant and is capable of expressing the full-length Tth DNA polymerase gene. The seed flask for a 10 liter fermentation contains tryptone (20 g/l), yeast extract (10 g/l), NaCl (10 g/l) and 0.005% ampicillin. The seed flask was inoculated from colonies from an agar plate, or a frozen glycerol culture stock can be used. The seed is grown to between 0.5 and 1.0 O.D. (A$_{680}$). The volume of seed culture inoculated into the fermentation is calculated such that the final concentration of bacteria will be 1 mg dry weight/liter. The 10 liter growth medium contained 25 mM KH$_2$PO$_4$, 28 mM (NH$_4$)$_2$ SO$_4$, 4 mM sodium citrate, 0.4 mM FeCl$_2$, 0.04 mM ZnCl$_2$, 0.03 mM CoCl$_2$, 0.03 mM CuCl$_2$, and 0.03 mM H$_3$BO$_3$. The following sterile components were added: 4 mM MgSO$_4$, 7.5 g/l glucose, and 20 mg/l thiamine-HCl. The pH was adjusted to 6.8 with NaOH and controlled during the fermentation by added NH$_4$OH. Glucose was continually added during the fermentation by coupling to NH$_4$OH addition. Foaming was controlled by the addition of polypropylene glycol as necessary, as an anti-foaming agent. Dissolved oxygen concentration was maintained at 40%.

The fermentation was inoculated as described above and the culture was grown at 30° C. until an optical density of 21 (A$_{680}$) was reached. The temperature was then raised to 37° C. to induce synthesis of rTth DNA polymerase. Growth continued for eight hours after induction, and the cells were then harvested by concentration using cross flow filtration followed by centrifugation. The resulting cell paste was frozen at −70° C. and yielded about 500 grams of cell paste. Unless otherwise indicated, all purification steps were conducted at 4° C.

Approximately 280 grams of frozen (−70° C.) E. coli K12 strain DG 116 harboring plasmid pLSG33 were warmed overnight to −20° C. To the cell pellet the following reagents were added: 1 volume of 2×TE (100 mM Tris-HCl, pH 7.5, 2 mM EDTA), 5 mg/ml leupeptin and 50 mg/ml PMSF. The final concentration of leupeptin was 0.5 µg/ml and for PMSF, 0.625 µg/ml. Preferably, beta-mercaptoethanol (2-Me) is included in TE to provide a final concentration of 5 mM 2-Me. The mixture was homogenized at low speed in a blender. All glassware was baked prior to use, and solutions used in the purification were autoclaved, if possible, prior to use. The cells were lysed by passage twice through a Microfluidizer at 10,000 psi.

The lysate was diluted with 1×TE containing 5 mM 2-Me to a final volume of 5.5× cell wet weight. Leupeptin was added to 0.5 µg/ml and PMSF was added to 0.625 µg/ml. The final volume (Fraction I) was approximately 1540 ml.

Ammonium sulfate was gradually added to 0.2M (26.4 g/l) and the lysate stirred. Upon addition of ammonium sulfate, a precipitate formed which was removed prior to the polyethylenimine (PEI) precipitation step, described below. The ammonium sulfate precipitate was removed by centrifugation of the suspension at 15,000–20,000×g in a JA-14 rotor for 20 minutes. The supernatant was decanted and retained. The ammonium sulfate supernatant was then stirred on a heating plate until the supernatant reached 75° C. and then was placed in a 77° C. bath and held there for 15 minutes with occasional stirring. The supernatant was then cooled in an ice bath to 20° C. and a 10 ml aliquot was removed for PEI titration.

PEI titration and agarose gel electrophoresis were used to determine that 0.3% PEI (commercially available from BDH as PolyminP) precipitates ≧90% of the macromolecular DNA and RNA, i.e., no DNA band was visible on an ethidium bromide stained agarose gel after treatment with PEI. PEI was added slowly with stirring to 0.3% from a 10% stock solution. The PEI treated supernatant was centrifuged at 10,000 RPM (17,000 ×g) for 20 minutes in a JA-14 rotor. The supernatant was decanted and retained. The volume (Fraction II) was approximately 1340 ml.

Fraction II was loaded onto a 2.6×13.3 cm (71 ml) phenyl sepharose Cl-4B (Pharmacia-LKB) column following equilibration with 6 to 10 column volumes of TE containing 0.2M ammonium sulfate. Fraction II was then loaded at a linear flow rate of 10 era/hr. The flow rate was 0.9 ml/min. The column was washed with 3 column volumes of the equilibration buffer and then with 2 column volumes of TE to remove non-Tth DNA polymerase proteins. The column was then washed with 2 column volumes of 20% ethylene glycol in TE to remove additional contaminating proteins. The recombinant Tth DNA polymerase was eluted with 4 column volumes of 2.5M urea in TE containing 20% ethylene glycol. The DNA polymerase containing fractions were identified by optical absorption ($A_{280}$) and SDS-PAGE according to standard procedures. Peak fractions were pooled and filtered through a 0.2 micron sterile vacuum filtration apparatus. The volume (Fraction III) was approximately 195 ml. The resin was equilibrated and recycled according to the manufacturer's recommendations.

A 2.6×1.75 cm (93 ml) heparin sepharose Cl-6B column (Pharmacia-LKB) was equilibrated with 6–10 column volumes of 0.15M KCl, 50 mM Tris-HCl, pH 7.5, 0.1 mM EDTA and 0.2% Tween 20™, at 1 column volume/hour. Preferably, the buffer contains 5 mM 2-Me. The column was washed with 3 column volumes of the equilibration buffer. The Tth DNA polymerase was eluted with a 10 column volume linear gradient of 150–750 mM KCl in the same buffer. Fractions (one-tenth column volume) were collected in sterile tubes and the peak was determined as for Fraction III. Recombinant Tth DNA polymerase eluted with a peak at 0.33M KCl. The peak fractions were pooled (Fraction IV, volume 177 ml).

Fraction IV was concentrated to 10 ml on an Amicon YM30 membrane. For buffer exchange, diafiltration was done 5 times with 2.5× storage buffer (50 mM Tris-HCl, pH 7.5, 250 mM KCl, 0.25 mM EDTA 2.5 mM DTT and 0.5% Tween-20™) by filling the concentrator to 20 ml and concentrating the volumes to 10 ml each time. The concentrator was emptied and rinsed with 10 ml 2.5× storage buffer which was combined with the concentrate to provide Fraction V.

Anion exchange chromatography was used to remove residual DNA. The procedure was conducted in a biological safety hood and sterile techniques were used. A Waters Sep-Pak plus QMA cartridge with a 0.2 micron sterile disposable syringe tip filter unit was equilibrated with 30 ml of 2.5× storage buffer using a syringe at a rate of about 5 drops per second. Using a disposable syringe, Fraction V was passed through the cartridge at about 1 drop/second and collected in a sterile tube. The cartridge was flushed with 5 ml of 2.5 ml storage buffer and pushed dry with air. The eluant was diluted 1.5× with 80% glycerol and stored at −20° C. The resulting final Fraction IV pool (57.5 mls) contained $16.1 \times 10^6$ units of activity.

VI. Annealing Procedure

For Examples II, III, and IV the cRNA template and DM156 primer were annealed at a 20:1 primer: template ratio in 10 mM Tris-HCl, pH 8.3, 50 mM KCl, 0.1 mM EDTA annealing buffer. To reduce pipeting errors and eliminate tube variations, a master mix was made to provide material for 80 reactions.

Annealing was accomplished as follows: the 80 reaction master mix was heated to 85°–87° C. for 4 minutes, then placed in a 70° C. water bath for 5 minutes, followed by a 60° C. water bath for 5 minutes and finally allowed to equilibrate at room temperature. The annealed mixture was then stored at 4° C. (or alternatively at −20° C.) for future use. For each reaction 2.5 µl of master mixture was used containing 0.5 pmol (0.175 µg) cRNA template and 10 pmoles primer. Alternatively, annealing was accomplished at 70° C. during incubation of the RT reaction.

VII. Determination of [α-$^{32}$P]dCMP Incorporation

The amount of isotope incorporated in the reverse transcribed product was measured by nucleic acid precipitation with trichloroacetic acid (TCA). This method is described in Maniatis et al., 1982, *Molecular Cloning*, Cold Spring Harbor Laboratory, page 473.

Example II

Analysis of AW106 cRNA as a Suitable Template for Reverse Transcription

The annealed AW106 cRNA:DM156 mixture was used as a template for reverse transcription with commercially available reverse transcriptase to test the suitability of AW106 cRNA as a template.

A 6× reaction mix was prepared containing 1× Pol I RT Buffer plus MgCl$_2$, 1× dNTP Stock, and 3 pmoles template annealed to 60 pmoles primer. This mix was aliquoted into six tubes. All reactions were set up at 0° C. As controls, one reaction was set up without template but with 10 units of MoMuLV-RT. Another reaction had no enzyme added. To the remaining reactions, MoMuLV-RT was added as follows: 10 units, 1 unit, 0.1 unit, and 0.01 unit.

All reactions were incubated at 37° C. for 20 minutes. The reactions were stopped by placing them in a 0° C. water ice/bath and adding EDTA to a final concentration of 10 mM. The [$\alpha$-$^{32}$P]dCMP incorporation was determined by measuring TCA precipitable counts.

The results shown in Table 1 demonstrated that AW106 cRNA was a suitable template for cDNA synthesis using MoMuLV-RT.

Example III

Comparison of E. coli Pol I and Taq Reverse Transcriptase Activities

Using the results of Example II as a standard, E. coli Pol I and nTaq polymerase were assayed for reverse transcriptase activity using AW 106 cRNA as a template. As positive controls, DNA templates were substituted for the cRNA template in one set of reactions. The results were quantitated as in Example II by measurement of [$\alpha$-$^{32}$P] dCMP incorporation.

A 12× Pol I master mix was prepared containing Pol I RT buffer minus MgCl$_2$ dNTP stock and 12 units Pol I enzyme. Similarly, a 12× Taq master mix was prepared containing Taq buffer, dNTP stock, and 12 units of native Taq enzyme and Taq diluent. The Pol I and Taq master mixes were divided to provide six reactions for the RNA template (0.5 pmoles cRNA/10 pmole DM156), two reactions for the DNA template (6.25 μg), and two control reactions with no template.

For the RNA template MnCl$_2$ or MgCl$_2$ was added to the six aliquots containing Pol I master mix plus cRNA/DM156 to achieve salt concentrations of 0, 0.5 mM MnCl$_2$, 0.7 mM MnCl$_2$, 1.0 mM MnCl$_2$, 2.0 mM MnCl2, and 6 mM MgCl$_2$. Six aliquots containing Taq master mix plus cRNA/DM 156 were supplemented with MnCl$_2$ or MgCl$_2$ so that the final salt concentration was 0, 0.5 mM MnCl$_2$, 0.7 mM MnCl$_2$, 1.0 mM MnCl$_2$, 2.0 mM MnCl$_2$, or 2 mM MgCl$_2$.

For the DNA template two aliquots were removed from the Pol I mix, and salt was added as to provide a final concentration of 0.7 mM MnCl$_2$ for one reaction and 6 mM MgCl$_2$ for the other. Two aliquots were removed from the Taq mix, and salt was added to provide a final concentration of 0.7 mM MnCl$_2$ for one reaction and 2 mM MgCl$_2$ for the other.

As negative controls, two reaction mixes were prepared for each of Pol I and Taq which lacked a template. These reactions were assembled using aliquots of the 12× Pol I and 12× Taq master mixes, and 1× annealing buffer was added in place of a template. For Pol I, salt was added to provide either 0.7 mM MnCl$_2$ or 6 mM MgCl$_2$. For Taq, salt was added to provide either 0.7 mM MnCl$_2$ or 2 mM MgCl$_2$.

All reactions were mixed on ice and then incubated at 37° C. for Pol I or at 65° C. for Taq. After 20 minutes the reactions were chilled on ice (0° C.) and EDTA was added to each reaction to a 10 mM final concentration. A sample was removed from each reaction to measure [$\alpha$-$^{32}$P]dCMP incorporation.

The results of this experiment are shown in Table I. All values shown are corrected for background.

TABLE I

|  | MoMuLV-RT (cpm) | nTaq (cpm) | E. coli Pol I (cpm) |
|---|---|---|---|
| minus template + 10 units enzyme | 90 | — | — |
| minus enzyme + template | 14 | — | — |
| 10 units enzyme + template | 7,825 | — | — |
| 1 unit enzyme + template | 3,263 | — | — |
| .1 unit enzyme + template | 924 | — | — |
| .01 unit enzyme + template | 170 | — | — |
| RNA template + 0 mM MnCl$_2$ | — | 9 | 0 |
| RNA template + .5 mM MnCl$_2$ | — | 256 | 7,561 |
| RNA template + .7 mM MnCl$_2$ | — | 3,088 | 6,666 |
| RNA template + 1 mM MnCl$_2$ | — | 3,977 | 7,508 |
| RNA template + 2 mM MnCl$_2$ | — | 2,696 | 1,558 |
| RNA template + 2 mM MgCl$_2$ | — | 73 | — |
| RNA template + 6 mM MgCl$_2$ | — | — | 760 |
| minus template + 6 mM MgCl$_2$ | — | — | 31 |
| minus template + .7 mM MnCl$_2$ | — | 5 | 28 |
| minus template + 2 mM MgCl$_2$ | — | 3 | — |
| DNA template + .7 mM MnCl$_2$ | — | 194,199 | 203,861 |
| DNA template + 6 mM MgCl$_2$ | — | — | 271,595 |
| DNA template + 2 mM MgCl$_2$ | — | 209,559 | — |

The data presented in Table I is presented graphically in FIG. 1.

This experiment demonstrates that Taq has reverse transcriptase activity. One unit of Taq is equivalent to 1 unit of MoMuLV reverse transcriptase by the amount of [$\alpha$-$^{32}$P] dCMP incorporated into a DNA transcript from an RNA template. E. coli Pol I also shows reverse transcriptase activity. Because Taq reactions were done at 65° C. rather than 37° C., product specificity is enhanced in the Taq reaction compared to either the Pol I or MoMuLV reverse transcriptase.

Example IV

Comparison of Reverse Transcriptase Activity in 94 kDA rTaq, 61 kDA rTaq and Tth Polymerase In order to determine whether the reverse transcriptase activity observed in Example III was common to other thermostable polymerases, the reverse transcription activity of 94 kDa Taq polymerase, Stoffel fragment (61 kDa, although previously referred to as 62 kDa Taq), and native Tth were compared. Both forms of Taq were produced by recombinant means.

A 2 μM dilution of 94 kDa Taq was prepared, assuming 94 μg/nmole, from a 23.4 μM stock solution. A dilution of the Stoffel fragment was similarly prepared using Taq diluent.

Both the 94 kDa and Stoffel fragment dilutions contained 0.36 pmoles/0.18 μl. Tth polymerase was purified as a 27 unit/μl solution with a specific activity of 80,000 units/mg. Therefore, 0.1 μl contained 0.36 pmole (2.7 units of enzyme). Reaction were set up with a final salt concentration of 60 mM KCl (HSB) or 15 mM KCl (LSB).

At 0° C. three 15× master mixes were prepared containing dNTP stock, enzyme diluent, and 5.4 pmoles enzyme (Tth, 94 kDa Taq, or Stoffel Fragment). From each 15× master mix six aliquots were combined with either HSB or LSB providing six reaction mixes for each of Tth/HSB, Tth/LSB, 94 kDa Taq/HSB, 94 kDa Taq/LSB, Stoffel Fragment/HSB and Stoffel Fragment/LSB.

For each of the six reaction mixes two separate aliquots were removed to tubes containing 1× annealing buffer for the minus template plus enzyme control reactions.

To the remaining five reactions worth of reaction mix, cRNA/DM156 annealed mix (3 pmoles template and 60 pmoles primer) was added. From each of the six series, four aliquots were removed to individual tubes. While still at 0° C., MnCl$_2$ was added to provide the final salt concentration show in Table II.

To determine background levels, minus-enzyme, minus-template controls were prepared containing 1× dNTP stock, 1× Annealing buffer, and 0×Taq diluent. The salts were adjusted as follows: HSB and a final MnCl$_2$ concentration of 0.6 mM or 1.2 mM, and LSB and a final MnCl$_2$ concentration of 0.6 mM or 1.2 mM.

All reaction mixes were incubated at 65° C. for 15 minutes. The tubes were then quenched in an ice bath and EDTA was added to each tube to a 10 mM final concentration. The amount of [α-$^{32}$P]dCMP incorporation was determined by TCA precipitation. The results are shown in Table II.

this experiment, the reverse transcriptase reaction was coupled to cDNA amplification by PCR. Recombinant Tth DNA polymerase was used as the thermostable polymerare for both the reverse transcriptase reaction and PCR. The cRNA template, prepared from plasmid pAW109 is described in Example 1(A). This embodiment of the invention excludes the pre-annealing step described in Example II and used in Examples III and IV.

The components for the RT reaction were combined at room temperature, in the following order: 9.4 μl, H$_2$O; 2 μl, 10× RT Reaction Buffer (100 mM Tris-HCl [pH 8.3], 900 mM KCl); 2 μl, 10 mM MnCl$_2$; 1.6 μl, dNTP solution (2.5 mM each dATP, dCTP, dGTP, dTTP in H$_2$O at pH 7.0); and 2 μl, rTth DNA polymerase (2.5 units/μl in 1× enzyme storage buffer containing 20 mM Tris-HCl [pH 7.5], 100 mM KCl, 0.1 mM EDTA 1 mM DTT, 0.2% Tween 20™ [Pierce Surfactamps] and 50% glycerol [v/v]). Although the

TABLE II

|  | 94 kDArTaq | | Stoffel Fragment (61 kDa Taq) | | Tth Pol | |
| --- | --- | --- | --- | --- | --- | --- |
|  | cpm | pmol | cpm | pmol | cpm | pmol |
| HSB | | | | | | |
| Minus template + 0.6 mM MnCl$_2$ | 0 | — | 0 | — | 10 | — |
| Minus template + 1.2 mM MnCl$_2$ | 0 | — | 0 | — | 6 | — |
| Plus template + 0.6 mM MnCl$_2$ | 517 | 5.04 | 34 | 0.332 | 1244 | 12.14 |
| Plus template + 0.8 mM MnCl$_2$ | 918 | 8.96 | 340 | 3.32 | 1981 | 19.33 |
| Plus template + 1.0 mM MnCl$_2$ | 1315 | 12.83 | 521 | 5.08 | 2178 | 21.25 |
| Plus template + 1.2 mM MnCl$_2$ | 1305 | 12.73 | 609 | 5.9 | 2369 | 23.11 |
| LSB | | | | | | |
| Minus template + 0.6 mM MnCl$_2$ | 7 | — | 0 | — | 234 | 2.28 |
| Minus template + 1.2 mM MnCl$_2$ | 18 | — | 0 | — | 2 | — |
| Plus template + 0.6 mM MnCl$_2$ | 276 | 2.69 | 81 | 0.79 | 618 | 6.03 |
| Plus template + 0.8 mM MnCl$_2$ | 1115 | 10.88 | 468 | 4.57 | 2263 | 23.06 |
| Plus template + 1.0 mM MnCl$_2$ | 1349 | 13.16 | 1068 | 10.46 | 2239 | 21.85 |
| Plus template + 1.2 mM MnCl$_2$ | 1061 | 10.35 | 898 | 8.76 | 2051 | 20.01 |

| Controls | |
| --- | --- |
| Minus Enzyme, Minus Template Reactions | cpm |
| 60 mM KCl 0.6 mM MnCl$_2$ | 19 |
| 60 mM KCl 1.2 mM MnCl$_2$ | 46 |
| 15 mM KCl 0.6 mM MnCl$_2$ | 11 |
| 15 mM KCl 1.2 mM MnCl$_2$ | 25 |

Input $^{32}$P for each reaction was 1.23×10$^6$ cpm. All numbers were corrected for average background of 37 cpm. The numbers reflect cpm incorporated per 12.5 μl of each reaction. Total pmoles of incorporation was calculated based on 984 cpm/pmole determined by counting $^{32}$P from an [α-$^{32}$P] dCTP stock solution.

Figure 2:
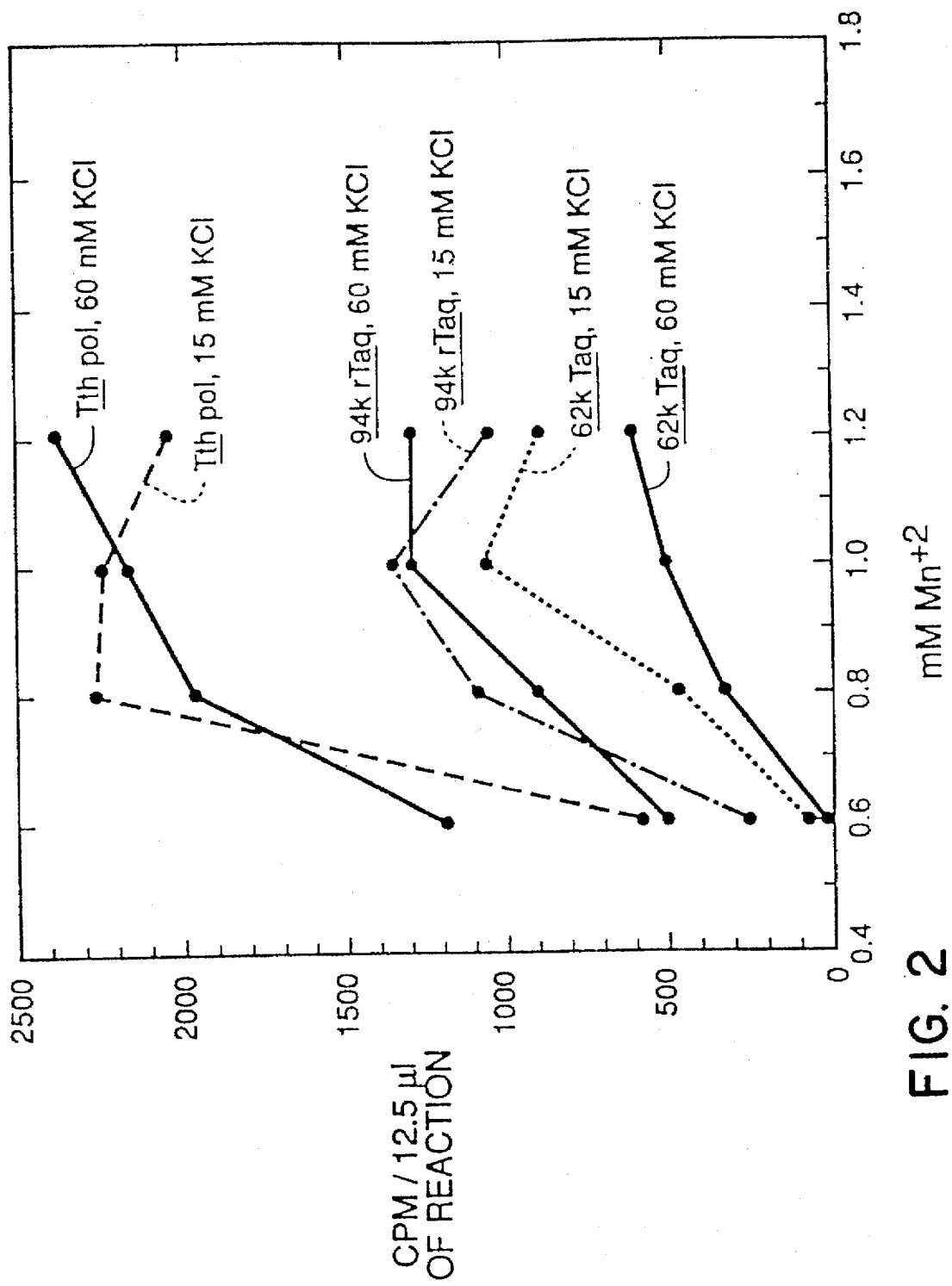
FIG. 2 is a graph comparing reverse transcription of an RNA-template, at varying $Mn^{+2}$ concentrations, catalyzed by Tth DNA polymerase, 94 kDa rTaq DNA polymerase, and AmpliTaq® DNA Polymerase, Stoffel Fragment (also referred to as 62 kDa rTaq).

These results are presented graphically in FIG. 2 and demonstrate that all thermostable DNA polymerases tested contain reverse transcriptase activity. The results of Examples III and IV indicate that the reverse transcriptase activity is not due to a contaminant because both native and recombinant forms of the thermostable DNA polymerases demonstrate this activity.

Example V

Procedure for High Temperature Reverse Transcription/Amplification

Examples III and IV demonstrate the ability of thermostable DNA polymerases to use an RNA template and produce a cDNA molecule, at an elevated temperature. In indicated volumes shown are intended as per reaction, for consistency and to avoid pipeting errors, the RT reaction mix was prepared as a 25× master mix. The 25× reaction master mix contained 425 μl (17 μl/Reaction).

RT-Primer mixes were prepared each as follows. 187 μl of RT mix was removed from the 25× RT master mix and combined with a "downstream" primer. This amount was sufficient for 11 RT reactions. Two RT-primer mixes were prepared each containing 187 μl RT reaction mix and 11 μl (1 μl per reaction) of either 15 μM DM152 (SEQ ID No. 11) (in water); or 15 μM TM01 (SEQ ID No. 12) (in water). Aliquotes comprising 18 μl of the DM152 RT-Primer mix were removed into tubes labeled 1–8. Similarly, 18 μl aliquotes of the TM01 (SEQ ID No. 12) RT-Primer mix were removed into tubes numbered 9–16.

Template AW109 cRNA was prepared as described in Example I, diluted, and added as a 2 μl template solution in TE (10 mM Tris-HCl, 1 mM EDTA), as shown below. The template solution contained 30 ng/μl rRNA as carrier.

| Tube Number | Copies of AW109 cRNA |
|---|---|
| 1, 9 | $10^8$ (-RT reaction) |
| 2, 10 | $10^8$ |
| 3, 11 | $10^6$ |
| 4, 12 | $10^4$ |
| 5, 13 | $10^3$ |
| 6, 14 | 500 |
| 7, 15 | 100 |
| 8, 16 | 0 |

Reaction tubes 2–8 and 10–16 were incubated at 70° C. for 2.5 minutes for DM152 (SEQ ID No. 11) and 7.5 minutes for TM01 (SEQ ID No. 12) samples. Tubes 1 and 9 were kept on ice as RT reaction negative controls to detect the presence of contaminating plasmid DNA that could later serve as a PCR template. After incubation at 70° C., the reactions were stopped by placing the tubes on ice.

The PCR assay mix was prepared at room temperature as a 19× master mix. The volumes shown are intended as volume per reaction: 71 µl $H_2O$; 8 µl 10× PCR Reaction Buffer (100 mM Tris-HCl [pH 8.3]; 1M KCl, 18.75 mM $MgCl_2$; 7.5 mM EGTA; 50% glycerol [v/v]) and 1 µl 15 µM DM151 (the "PCR upstream primer" in $H_2O$). The total volume was 80 µl per reaction.

The PCR amplification was initiated by adding the 80 µl PCR assay mixture to the 20 µl reverse transcriptase reaction. A mineral oil overlay (75 µl) was added to prevent evaporation and the mix was then spun in a microcentrifuge for approximately 20 seconds to separate the oil layer from the reaction mix. PCR was conducted using a thermal cycler (Perkin Elmer, Norwalk, Conn.) and four linked files as follows:

File 1—Step Cycle 2 minute at 95° C. for 1 cycle

File 2—Step Cycle 1 minute at 95° C. and 1 minute at 60° C. for 35 cycles

File 3—Step Cycle 7 minute at 60° C. for 1 cycle

File 4—Soak 4° C.

Following PCR, 5 µl aliquots were removed from each sample and combined with 5 µl sample dye (30% w/v sucrose, 0.1% w/v bromophenol blue, 10 mM EDTA) analyzed on an agarose-gel (2% NuSieve® GTG agarose [FMC], 1% Seakem® ME agarose [FMC]). Following electrophoresis, the gel was stained with ethidium bromide and photographed (see FIG. 3). All product lengths were determined relative to a 1 kb BRL molecular weight standard (lane not shown). In the figure, the lane numbers correspond to tube numbers. The expected product, 308 bp in length, was visible at 100 copies AW109 cRNA per reaction. When TM01 (SEQ ID No. 12) was used to produce a 730 bp transcription/amplification product, the correct size band was visible at 100 molecules of template per reaction. No PCR product was detected in the negative control reactions.

Example VI

Coupled Reverse Transcription/Amplification Using Total Cellular RNA

The K562 cell line was used as a source of total cellular RNA. The RNA was purified as described in Example I. The purpose of this experiment was to examine the sensitivity of the coupled RT/PCR procedure using a naturally occurring heterogeneous RNA composition. Generally, it can be assumed that 250 ng of total RNA per reaction represents approximately 25,000 cells. Each cell contains approximately 1–10 copies of IL-1α mRNA. Therefore, 250 ng of K562 total RNA contains roughly 25,000 to 250,000 copies of IL-1α target mRNA. Thus, the specificity and amount of PCR product can be compared to the specificity and amount of product made using the synthetic cRNA template in Example V.

The reaction conditions were as described in Example V using DM151 (SEQ ID No. 10) and DM152 (SEQ ID No. 11) with a few minor changes described below. Because only one downstream primer was used in this experiment, DM152 (SEQ ID No. 11) was added directly to the RT reaction mix. A 10× RT reaction master mix was prepared containing, for each reaction, 9 µl $H_2O$; 2 µl 10× RT Reaction Buffer; 2 µl 10 mM $MnCl_2$; 2 µl dNTP (2 mM each dATP, dCTP, dGTP, and dTTP in $H_2O$, pH 7.0) and 1 µl DM152 (SEQ ID No. 11) (15 µM in water). The RT master mix was prepared at room temperature and 16 µl aliquots were dispensed into tubes numbered 1–8 containing RNA as shown below.

| Tube Number | K562 Total RNA |
|---|---|
| 1 | 250 ng (-RT control) |
| 2 | 250 ng |
| 3 | 50 ng |
| 4 | 10 ng |
| 5 | 2 ng |
| 6 | 0.4 ng |
| 7 | 0.08 ng |
| 8 | 0 ng |

All template solutions were in TE (10 mM Tris-HCl, 1 mM EDTA). Two µl of template solution and 2 µl of Tth DNA polymerase (2.5 units/µl in 1× enzyme storage buffer) were added to each tube.

All samples were incubated at 70° C. for 2.5 minutes with the exception of tube 1 which was kept on ice as a negative RT control to test for the presence of contaminating DNA that might serve later as a PCR template. The reactions were stopped by placing them on ice.

The PCR assay mix was prepared, and the reaction was carried out exactly as described in Example V. The RT/PCR results were analyzed as in Example V, and the results are shown in FIG. 4. A PCR product band was visible in lanes 2–7. The results, shown in FIG. 4, demonstrate that as little as 80 picograms of total cellular RNA (corresponding to 8 cell equivalents of total RNA or 8–80 copies of IL-1α mRNA) serves as an excellent template for specific and efficient high temperature reverse transcription and amplification according to the methods of the present invention.

Example VII

Procedure for High Temperature Reverse Transcription/Amplification Wherein the Polymerase is Exchanged Example IV suggests that Tth DNA polymerase may be superior to Taq DNA polymerase for preparing cDNA. However, Taq DNA polymerase is frequently used in PCR. Therefore, a procedure was developed wherein Tth DNA polymerase catalyzes the RT reaction and Taq DNA polymerase catalyzes PCR. The following procedure is suitable when the two reactions are catalyzed by different thermostable DNA polymerases or when the amount of polymerase in the RT reaction is decreased for PCR.

As an illustration, the following experiment was carried out. Generally, the RT reaction was carried out as in Example V, however, for half of the reaction tubes, the Tth DNA polymerase was heat killed and replaced with Taq DNA polymerare for PCR.

The specific protocol was as follows. The RT master mix was prepared, with DM152 (SEQ ID No. 11), exactly as described in Example VI. The RT master mix was made up as a 9× mix. Sixteen µl aliquots were removed into tubes numbered 1-8 containing AW109 cRNA or pAW109 DNA as shown below.

Template solutions were all prepared as 2 µl samples in TE as in Example V. Two µl of rTth DNA polymerase was added to each of tubes 1–8 (2.5 units/µl in 1× enzyme storage buffer) and the RT reactions were incubated at 70° C. for 2.5 minutes, with the exception of tubes 1, 2, 5, and 6. These tubes were kept on ice as RT reaction negative controls. The reactions were stopped by placing the tubes on ice. The table below summarizes the reaction conditions for each tube.

| Lane | Sample | RT Reaction Temp. | PCR Enzyme |
|------|--------|-------------------|------------|
| 1 | $10^4$ copies DNA | 0° C. | rTth |
| 2 | $10^4$ copies cRNA | 0° C. | rTth |
| 3 | $10^4$ copies cRNA | 70° C. | rTth |
| 4 | — | 70° C. | rTth |
| 5 | $10^4$ copies DNA | 0° C. | Taq |
| 6 | $10^4$ copies cRNA | 0° C. | Taq |
| 7 | $10^4$ copies cRNA | 70° C. | Taq |
| 8 | — | 70° C. | Taq |

At room temperature, two PCR master mixes were prepared. PCR minus Taq contained, per reaction, 71 µl $H_2O$, 8 µl 10× PCR reaction buffer (100 mM Tris-HCl, pH 8.3; 1M KCl; 18.75 mM $MgCl_2$, 7.5 mM EGTA, 50% glycerol [w/v]) and 1 µl DM151 (15 µM in water). The PCR minus Taq mix was prepared as a 5× solution. A PCR plus Taq master mix was also prepared as a 5× solution containing, per reaction, 68.5 µl $H_2O$; 8 µl 10× Taq-PCR reaction buffer (100 mM Tris-HCl, pH 8.3; 300 mM KCl; 25 mM $MgCl_2$), 1 µl DM151, and 0.5 µl AmpliTaq® DNA Polymerase (5 units/ µl).

Eighty µl of PCR minus Taq master mix were added to tubes 1-4. EGTA (2 µl of 30 mM stock) was added to tubes 5-8. Mineral oil was then added to all tubes (75 µl/tube). Tubes 5-8 were heated to 99° C. for 4 minutes, and 78 µl of PCR plus Taq reaction mix was added to those tubes only (below the oil level). All tubes were spun in a microcentrifuge for approximately 20 seconds and incubated in a thermal cycler using the four linked files described in Example V. The RT/PCR amplifications were analyzed by electrophoresis as described in Example V, and the gel was photographed (FIG. 5). FIG. 5 demonstrates that replacement of rTth DNA polymerase with AmpliTaq® DNA Polymerase in the PCR step does not effect product yield.

Example VIII

Comparison of Taq Polymerase and Tth Polymerase in a Coupled RT/PCR Reaction

The use of the cRNA standard described in Example VII facilitates direct analysis of the effect of experimental conditions on RT/PCR efficiency, because the number of target molecules present in the reaction mix is known. Specifically, the efficiency of Tth and Taq DNA polymerases in a coupled RT/PCR reaction were compared.

RT reactions (20 µl) contained 10 mM Tris-HCl, pH 8.3; 90 mM KCl (40 mM for reactions containing Taq); 1.0 mM $MnCl_2$; 200 µM each of dATP, dCTP, dGTP, and dTTP; 15 pmol of DM152 (SEQ ID No. 11) and 5 units of rTth or Taq DNA polymerase, and $10^6$, $10^5$, or $10^4$ copies of pAW109 cRNA. The six reactions were overlaid with 75 µl mineral oil and incubated for 15 minutes 70° C.

Following the RT reaction, 80 µl of a solution containing 10 mM Tris-HCl (pH 8.3), 100 mM KCl (50 mM for reactions containing Taq), 1.88 mM $MgCl_2$, 0.75 mM EGTA, 5% glycerol [v/v], and 15 pmol of primer DM151 was added. The samples (100 µl) were then amplified in a Perkin Elmer, Norwalk, Conn., Thermal Cycler as follows: 2 minutes at 95° C. for 1 cycle; 1 minute at 95° C. and 1 minute at 60° C. for 35 cycles; and 7 minutes at 60° C. for 1 cycle. Aliquots (5 µl) of the PCR amplifications were analyzed by electrophoresis on 2% (w/v) NuSieve® 1% (w/v) Seakem® agarose stained with ethidium bromide.

Results

The rTth DNA polymerase generated a 308 bp product visualized by ethidium bromide stained gel electrophoresis starting with $10^4$ copies of target cRNA. Product was not observed for the Taq polymerase at $10^4$ or $10^5$ copies of target, although lower limits of detection would be expected if hybridization techniques were used rather than ethidium bromide staining. These results demonstrated that under similar reaction conditions the Tth DNA polymerase provides approximately 100-fold greater sensitivity than the analogous Taq DNA polymerase in a coupled reverse transcription PCR amplification.

Example IX

Preferred Non-Homogeneous Reverse Transcription/PCR Protocol

A. Reverse Transcription Reaction

In a 0.5 ml polypropylene microcentrifuge tube combine 9.4 µl sterile distilled water; 2 µl 10× rTth RT buffer; 2 µl $MnCl_2$ (10 mM); 0.4 µl of each of dGTP, dATP, dTTP, and dCTP (each at 10 mM); 2 µl rTth DNA polymerase 2.5 U/µl; 1 µl of primer DM152 (SEQ ID No. 11) (15 µM) (or an alternative "downstream" primer); and 2 µl positive control RNA or experimental sample containing ≦250 ng total RNA.

In this embodiment, the positive control RNA serves as template for DM152 (SEQ ID No. 11). The control RNA concentration is preferably ~$10^4$ copies/20 µL. For example, the control RNA may be RNA transcribed from pAW109 in 30 µg/ml *E. coli* rRNA in 10 mM Tris-HCl, pH 8.0, 1 mM EDTA and 10 mM NaCl.

The total reverse transcription reaction volume should be 20 µl per sample.

To reduce evaporation or refluxing, overlay the mix with 50–100 µl mineral oil.

Incubate the tubes in a Perkin-Elmer, Norwalk, Conn., thermal cycler using a soak file at 70° C. for 5–15 minutes. Stop the reaction by placing the tubes on ice until needed.

B. PCR Reaction

For each sample prepare a minimum of 80 µl of PCR master mix as follows: 8 µl 10× chelating buffer, 6–10 µl 25 mM $MgCl_2$, 1 µl primer DM151 (SEQ ID No. 10) (15 µM) or experimental "upstream" primer and sterile distilled water. Any combination of water, $MgCl_2$ and "upstream" primer volumes can be used as long as the total volume of the master mix equals 80 µl per sample.

The optimal $MgCl_2$ concentration may vary, depending on the total dNTP concentration, and the primer and template used. In most cases a final concentration of $MgCl_2$ in the range of 1.5–2.5 mM in the reaction mix will provide excellent results. If the template used is the positive control pAW109 RNA, 6 µl of 25 mM MgCl$_2$ stock solution is preferred for final 1.5 mM MgCl$_2$ concentration.

Dispense 80 µl of the PCR master mix into each reverse transcription reaction tube. Change pipet tips between additions to avoid sample carryover. Centrifuge the tubes for ~30 seconds in a microcentrifuge.

For amplification of the pAW109 RNA positive control, the thermal cycler (Perkin Elmer, Norwalk, Conn.) is programmed for four linked files as follows:

| | |
|---|---|
| Step Cycle: | 2 minutes at 95° C. for 1 cycle |
| Step Cycle: | 1 minute at 95° C. and 1 minute at 60° C. for 35 cycles |
| Step Cycle: | 7 minutes at 60° C. for 1 cycle |
| Soak: | 4° C. |

The PCR amplified samples can be stored frozen until subsequent analysis.

The selection of 60° C. for the anneal-extend temperature is optimal for amplification of the positive control cDNA. It may be necessary to lower or raise the anneal-extend temperature for other primer-template pairs. Higher anneal-extend temperatures generally result in improved product specificity (see Saiki et al., 1988, Science 239:487–491, incorporated herein by reference). The optimum can be determined empirically by testing at 5° C., or smaller, increments until the maximum in specificity and product yield is reached.

The optimal magnesium chloride concentration for PCR amplification can be determined empirically by testing concentrations from 1.5 to 2.5 mM magnesium chloride for each primer set. Too little or too much magnesium chloride may effect amplification efficiency. It may be preferable to adjust the magnesium chloride concentration in parallel with substantial changes in the concentration of sample RNA, dNTPs, cDNA, and DNA.

For templates known to contain a high amount of secondary structure, a "hot start" protocol may be preferred. Two reaction mixes for the reverse transcription reaction are prepared. Mix A: 9.4 µl sterile distilled water; 2 µl 10× rTth reverse transcriptase buffer; 1 µl "downstream primer;" 2 µl sample RNA (<250 ng of total RNA). Mix B: 2 µl, 10 mM MnCl$_2$ solution; 0.4 µl dGTP; 0.4 µl dATP; 0.4 µl dCTP; 0.4 µl dTTP (each at 10 mM); 2 µl rTth DNA polymerase.

Prepare both reaction mixes at room temperature. Incubate Mix A for 5 minutes at 70° C., add reaction Mix B (while reaction Mix A is still at 70° C.) and incubate for 5 to 15 minutes at 70° C. as described above in the section entitled "Reverse Transcription Reaction." Run the PCR reaction as described above.

C. Reagents

The preferred protocol utilizes the following reagents:

| | |
|---|---|
| rTth DNA polymerase | 2.5 Units/µl |
| Primer DM152 (SEQ ID No. 11) | 15 µM |
| Primer DM151 (SEQ ID No. 10) | 15 µM |
| Positive Control RNA | 5 × 10$^3$ copies/µl |
| dATP | 10 mM |
| dGTP | 10 mM |
| dCTP | 10 mM |
| dTTP | 10 mM |
| 10X rTth Reverse Transcriptase RT Buffer: | 100 mM Tris-HCl pH 8.3, 900 mM KCl |
| 10X Chelating Buffer: | 50% glycerol (v/v) 100 mM Tris-HCl, pH 8.3, 1M KCl, 7.5 mM EGTA, 0.5% Tween 20 |
| MnCl$_2$ Solution | 10 mM |
| MgCl$_2$ Solution | 25 mM |

These components may be assembled as a kit for high temperature reverse transcription. Variations to the kit are within the scope of the disclosed invention. For example, MnCl$_2$ may be included in the reverse transcriptase buffer and MgCl$_2$ may be included in the Chelating buffer. However, for optimization of the reactions MnCl$_2$ and MgCl$_2$ are provided as separate reagents. The use of a positive control, while not essential, is preferred in a commercial embodiment of the invention.

Example X

Homogeneous RT/PCR Assay

This method provides a procedure for a two-step, single addition reverse transcription/PCR amplification reaction. A TC9600 thermal cycler (Perkin Elmer, Norwalk, Conn.) was used and the instrument was turned on, to preheat the cover, prior to preparing the reaction mixture. Reactions were carried out in 0.2 ml MicroAmp® tubes, commercially available from Perkin Elmer, Norwalk, Conn. Each reaction contained 6.4 µl sterile distilled H$_2$O; 2 µl 10× RT buffer (100 mM Tris-HCl, pH 8.3; 900 mM KCl); 1.6 µl of 10 mM MnCl$_2$; 2 µl of 10× dNTP-T (2 mM each dATP, dCTP, dGTP in H$_2$O pH7.0); 2µl of 2mM dTTP; 1 µl of primer DM152 (SEQ ID No. 11) (15 µM); 1 µl of primer DM151 (15 µM); and 2 µl rTth DNA polymerase (2.5 U/µl). A 20× reaction mixture was made up (360 µl total volume) and 18 µl of the mixture was aliquoted into 16 tubes containing template as described below. The template used was AW109 cRNA. Tube Nos. 1–3 and 9–11 contained 10$^4$ copies of template in 2 µl. Tube Nos. 4–6 and 12–14 each contained 10$^2$ copies in 2 µl. Tube Nos. 7, 8, 15, and 16 contained only 2 µl of 30 ng/µl rRNA as a negative control.

Tube Nos. 1–8 were kept on ice during the RT reaction as −RT controls. Tube Nos. 9–16 were placed in a TC9600 thermal cycler (Perkin Elmer, Norwalk, Conn.) and heated for 1 cycle at 70° C. for 15 minutes and then heated to 95° C. while Tube Nos. 1–8 were placed in the thermal cycler for the PCR step. All tubes were cycled as follows:

75 seconds 95° C. 1 cycle 30 seconds 95° C., 20 seconds 60° C. for 35 cycles 2 minutes 60° C. 1 cycle Results Five µl of each reaction was then analyzed on a 2% NuSieve 1% agarose gel, stained with ethidium bromide and photographed. No product of the predicted size was visible in the −RT controls (Tube Nos. 1–8) or the "no target controls" (Tube Nos. 15 and 16). Product of the expected size was readily visible in lanes 9–11 (10$^4$ copies of target) and also present in lanes 12–14 (10$^2$ copies of target), although, expectedly, with less intensity.

Example XI

Utilization of dUTP and Uracil-N-Glycosylase (UNG) as a Carryover Prevention During High Temperature Reverse Transcription and Amplification This example illustrates the incorporation of an unconventional nucleotide to minimize carryover contamination. The reaction mix was treated with UNG prior to reverse transcription to degrade contaminating products from previous assays containing the same unconventional nucleotide. UNG treatment is as follows: 0.5 units UNG (developed and manufactured by Hoffmann-La Roche Inc. and commercially available from Perkin Elmer, Norwalk, Conn.) per 20 μl RT reaction. The reaction was incubated for 10 minutes at room temperature followed by heating at 70° C. for 15 minutes to inactivate the glycosylase and allow for reverse transcription. The experiment also demonstrates $MnCl_2$ concentration titration for determining the optimum concentration for the particular target, primers, and reaction conditions shown. The cDNA is then amplified by a PCR.

An 8× RT reaction mixture was prepared that contained: 48 μl sterile DEPC-treated distilled water; 16 μl 10× RT Buffer (100 mM Tris-HCl, pH 8.3; 900 mM KCl); 16 μl of a dNTP mix containing 2 mM each of dATP, dCTP, dGTP, and dUTP; 16 μl each of DM152 (SEQ ID No. 11) (1.5 μM) and DM151 (SEQ ID No. 10) (1.5 μM); 16 μl of AW109 cRNA template ($5×10^3$ copies/μl); and 16 μl of rTth DNA polymerase (2.5 units/μl). The final volume was 144 μl (18 μl/reaction). A 7× PCR master mixture was prepared that contained: 297 μl sterile DEPC-treated distilled water; 56 μl 10× PCR buffer (100 mM Tris-HCl, pH 8.3; 1M KCl; 7.5 mM EGTA; 50% glycerol [v/v]); 140 μl 10 mM $MgCl_2$; 56 μl dNTP mix containing 2 mM each of dATP, dCTP, dGTP, dUTP; 5.6 μl of each of DM152 and DM151 (SEQ ID Nos. 11 and 10) (15 μM). The final volume was 560 μl, 80 μl per reaction.

Eighteen μl of the RT mix was aliquoted into six sterile microcentrifuge tubes and $MnCl_2$ added in a 2 μl volume to provide a final $MnCl_2$ concentration as follows: Tube Nos. 1 and 2 (1.2 mM $MnCl_2$); Tube Nos. 3 and 4 (1.0 mM $MnCl_2$); and Tube Nos. 5 and 6 (0.8 mM $MnCl_2$). A mineral oil overlay (75 μl) was added to each tube and the reactions were incubated at 70° C. for 15 minutes in a water bath. Following the 70° C. incubation, 80 μl of the PCR master mix was added to each. The reaction tubes were thermocycled as follows: 2 minutes at 95° C. for 1 cycle; 1 minute at 95° C. and 1 minute at 60° C. for 35 cycles; 7 minutes at 60° C. for 1 cycle; and soak at 4° C.

Results

Five μl of each reaction mix was electrophoresed on a 2% NuSieve 1% agarose gel. The gel was stained and photographed. PCR product of the expected size was clearly visible in samples from all three $MnCl_2$ concentrations. The product yield increased with increasing $MnCl_2$ concentration.

Example XII

Procedure for Sterilization of a Homogeneous RT/PCR Assay

This example illustrates a method for sterilization of a homogeneous RT/PCR reaction contaminated with nucleic acids generated from a previous reaction. The reaction mix is treated with UNG prior to reverse transcription.

The unconventional nucleotide, dUTP, is incorporated during the RT/PCR reaction. Consequently, any product DNA present as a contaminant in subsequent reactions can be hydrolyzed using UNG.

In a 0.2 ml MicroAmp® tube combine 5.5 μl sterile distilled water; 2 μl 10× RT buffer (100 mM Tris-HCl, pH 8.3; 900 mM KCl); 2 μl of 8 mM $MnCl_2$; 2 μl dNTP mix containing 2 mM each of dATP, dCTP, dGTP, and dUTP; 2 μl each of DM152 (SEQ ID No. 11) (1.5 μM) and DM151 (SEQ ID No. 10) (1.5 μM); 2 μl of AW109 cRNA template ($5×10^3$ copies/μl); 0.5 μl UNG (1 unit/μl); and 2 μl of rTth (2.5 units/μl). The reaction is incubated for 10 minutes at room temperature and subsequently heated at 70° C. for 15 minutes to inactivate the glycosylase prior to reverse transcription. The cDNA is then amplified by a PCR.

In this example, the positive control RNA serves as a template for DM152 (SEQ ID No. 11) and DM151 (SEQ ID No. 10) is the upstream primer. The total reaction volume is 20 μl/sample. Incubate the tubes in a Thermal Cycler (for example, a TC9600 thermal cycler [Perkin Elmer, Norwalk, Conn.]) as follows:

70° C. for 15 minutes for 1 cycle

95° C. for 15 seconds and 60° for 20 seconds for 2 cycles

90° C. for 15 seconds and 60° C. for 20 seconds for 33 cycles

60° C. for 4 minutes for 1 cycle

The optimal manganese concentration may vary depending on the particular sample, target, primers, and the dNTP concentration in the reaction mixture.

Example XIII

Additional Template Nucleic Acids

Additional RNA and DNA templates were used in the experiments described in the Examples, below.

I. pTM3

The plasmid pTM3 is a 7821 nucleotide circular single stranded DNA with approximately 700 nucleotides of pAW109 DNA present. This provides a DNA template with the same sequence and primer binding site as the pAW109 cRNA. When transcribed using primer MT24 (SEQ ID No. 13), the first 253 nucleotides are identical to pAW109 cRNA. Beyond that region, the DNA becomes G+C rich and comprises DNA from *Thermus aquaticus*, including the gene for the Taq DNA polymerase. The pTM3 plasmid was constructed using the following protocol using techniques well known in the art (see Sambrook (see Sambrook et al., *Molecular Cloning—A Laboratory Manual*, Cold Spring Harbor Laboratory, Cold Spring Harbor, N.Y., 1989, incorporated herein by reference).

The insert was prepared by linearizing pAW109 DNA, described above, with BamHI. Linker adapters MT20 (SEQ ID No. 14) and MT21 (SEQ ID No. 15) were annealed to the linearized pAW109 DNA and ligated. These linkers anneal to the BamHI site. The fragment was digested with EcoRI and the resulting 706 bp fragment was gel purified.

The expression vector pLSG1 is described in U.S. Pat. No. 4,889,818, which is incorporated herein by reference, and contains the gene encoding the Taq DNA polymerase. The plasmid pLSG1 was linearized with EcoRI, mixed with an excess amount of gel purified fragment, and ligated to the fragment. The resulting plasmid was transformed into DG98 and single-stranded DNA was isolated with a helper phage (described in U.S. Pat. Nos. 4,889,818 and 5,079,352 and Lawyer et al., 1993, supra.).

The oligonucleotide sequences used in the above reactions are provided below.

| Oligo | SEQ ID No. | Sequence |
|---|---|---|
| MT24 | 13 | 5'-CAGGTCTCCCAAGTCTGGCGCCCTGCAAATGAGACACTTTCTCG-3' |
| MT20 | 14 | 5'-GATCTCCGGACTCTAGA-3' |
| MT21 | 15 | 5'-AATTTCTAGAGTCCGGA-3' |

II. HCV

HCV RNA transcript was generated as described in Young et al., 1993, *J. Clin. Microbiol.* 31:882–886, which is incorporated herein by reference. The cDNA clone was designated therein as pHCV1.1A. Preferred primers for the amplification of HCV templates are KY78 (SEQ ID No. 16; 5'-CTCGCAAGCACCCTATCAGGCAGT-3') and KY90 (SEQ ID No. 17; 5'-GCAGAAAGCGTCTAGCCATGGCGT-3'). KY78 (SEQ ID No. 16) and KY90 (SEQ ID No. 17) are biotinylated at the 5' end; KY80 (SEQ ID No. 17) is a non-biotinylated version of KY90 (SEQ ID No. 17).

III. HIV

A template was designed with primer binding regions identical to HIV-1 and an internal region flanked by the primer binding sites with a nucleotide sequence that, while maintaining the same base composition, differed from the corresponding HIV-1 sequence sufficiently to allow detection by a unique sequence specific probe. Preferred primers for the amplification of HIV templates are the 5'-biotinylated derivatives of SK431 (SEQ ID No. 6) and SK462 (SEQ ID No. 5), described above.

The template was generated by the annealing and extension of two oligonucleotides that overlap by 8 bases of complementarity at the 3' termini. The constituent oligonucleotides can be synthesized by any of the means for synthesizing oligonucleotides described above. The first oligonucleotide, SK550 (SEQ ID No. 18), contains a SalI linker and a SK462 (SEQ ID No. 5) primer binding region. The second oligonucleotide, SK551 (SEQ ID No. 19), contains a SK431 (SEQ ID No. 6) primer binding region. Synthesis of the control template was carried out using techniques well known in the art (see Sambrook et al., 1989, supra.).

The reaction mixture for the annealing and extension reaction was as follows:

- 7 µl of 10× Polymerase buffer (100 mM Tris-HCl at pH 7.5, 500 mM sodium chloride (NaCl), 100 mM magnesium acetate [Mg(OAc)$_2$]).
- 50 pmoles SK550 (SEQ ID No. 18)
- 50 pmoles SK551 (SEQ ID No. 19)
- 15 µl of each dATP, dGTP, dCTP, dTTP (10 mM stock solutions)
- 1 µl Klenow Fragment (5 U)
- H$_2$O to 70 µl The two oligonucleotides were mixed and held on ice for 10 minutes to allow the 3' termini of each oligonucleotide to anneal. The extension reaction was carried out for 30 minutes at room temperature followed by 30 minutes at 37° C. Following extension, the reaction mixture was held at 72° C. for 10 minutes to inactivate the polymerase.

The extended products were digested with SalI, which cleaves the SK550 (SEQ ID No. 18) end of the duplex sequence; the SK551 (SEQ ID No. 19) end remains blunt. The resulting fragment was cloned into the SalI and SmaI sites of the transcription vector pSP64 (Promega, Madison, Wis.) (with poly A), resulting in plasmid pNAS-2.

Following isolation and purification, pNAS-2 was linearized by digestion with EcoRI and transcribed in vitro with SP6 RNA polymerase. To remove residual DNA, the RNA was digested with RNase-free DNase and passed through an oligo-dT column.

The nucleotide sequences used in the above reactions are provided below.

| Oligo | SEQ ID No. | Sequence |
|---|---|---|
| SK550 | 18 | 5'-CGCGTCGACAGTTGGAGGACATC AAGCAGCCATGCAAATGTTAAAACATAGC ACTATAGAACTCTGCAAGCCTCGAGTG-3' |
| SK551 | 19 | 5'-GATCCTGCTATGTCAGTTCCCCTTGGT TCTCTCATCTGGCCTGGTGCAAT AGGCCCTGCATGCACTGGCACTCTCACT CGAG-3' |

Example XIV

Manganese Concentration Range

Extension reactions using RNA and DNA templates in either a Bicine or a Tris buffer were performed to determine the usable range of $Mn^{+2}$ concentrations for each reaction. A series of $Mn^{+2}$ concentrations for extension reactions with a DNA template and extension reactions with an RNA template were used. All reactions were carried out at 60° C. for 10 minutes in a 20 µl total volume. Reaction conditions were as follows:

RNA template, Bicine Buffer
- 3×10$^{11}$ copies pAW109 cRNA
- 0.125 µM MT24 (SEQ ID No. 13)
- 300 µM each dATP, dCTP, dGTP, dTTP
- 50 mM Bicine-KOH (pH 8.3)
- 100 mM KOAc (pH 7.5)
- Mn(OAc)$_2$ (1–20 mM, 1–6 mM shown)
- 5 U rTth* DNA polymerase RNA template, Tris Buffer
- 3×10$^{11}$ copies pAW109 cRNA
- 0.125 µM MT24 (SEQ ID No. 13)
- 200 µM each dATP, dCTP, dGTP, dTTP
- 10 mM Tris-HCl (pH 8.3)
- 90 mM KCl
- MnCl$_2$ (0.4–2.5 mM)
- 5 U rTth* DNA polymerase DNA template, Bicine Buffer
- 1.5×10$^{11}$ copies pTM3 ss DNA
- 0.0625 µM MT24 (SEQ ID No. 13)
- 300 µM each dATP, dCTP, dGTP, dTTP
- 50 mM Bicine-KOH (pH 8.3)
- 100 mM KOAc (pH 7.5)
- Mn(OAc)$_2$ (1–5 mM)
- 0.15 U rTth* DNA polymerase DNA template, Tris Buffer
- 1.5×10$^{11}$ copies pTM3 ss DNA
- 0.0625 µM MT24 (SEQ ID No. 13)

200 μM each dATP, dCTP, dGTP, dTTP
10 mM Tris-HCl (pH 8.3)
90 mM KCl
MnCl₂ (0.4–2.5 mM)
0.15 U rTth* DNA polymerase

*Developed and manufactured by Hoffmann-La Roche Inc. and commercially available from Perkin Elmer, Norwalk, Conn.

Figure 6:
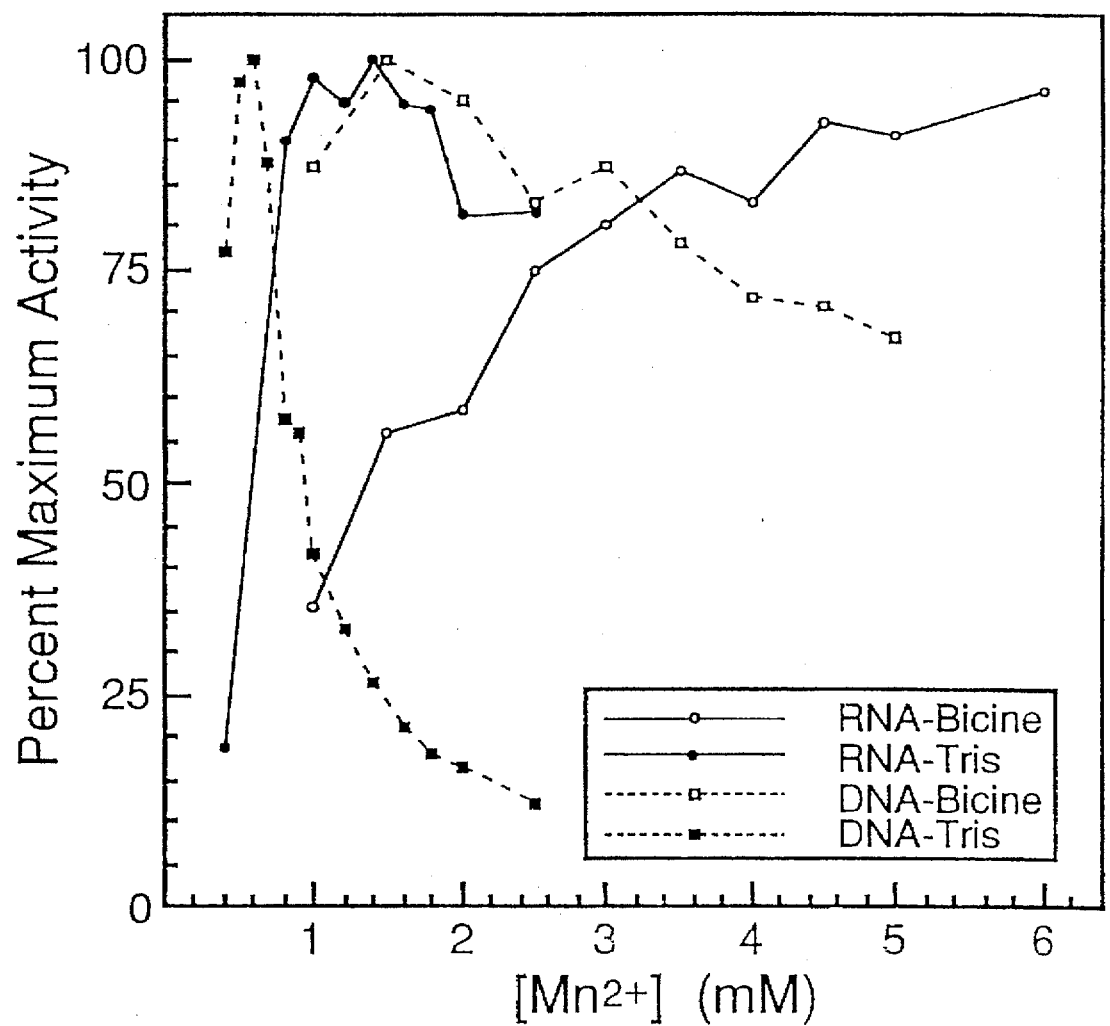
FIG. 6 depicts the results of extension reactions described in Example XIV, wherein the reaction efficiency is assayed over a range of manganese concentrations using different buffer conditions.

The amount of dNMP incorporated was assayed as described in Myers and Gelfand, 1991, supra., which is incorporated herein by reference. The results are shown in FIG. 6. The amount of dNMP incorporated is presented as a percentage of the maximum amount incorporated for each reaction. The maximum amount incorporated for each reactions is given below.

| Template | Buffer | 100% Activity |
|---|---|---|
| RNA | Bicine | 98 pmol dNMP incorporated |
| RNA | Tris | 87 pmol dNMP incorporated |
| DNA | Bicine | 166 pmol dNMP incorporated |
| DNA | Tris | 173 pmol dNMP incorporated |

Using the Tris buffer, the manganese concentration providing optimal synthesis with DNA templates was found to be approximately 0.6 mM, the enzyme obtained maximal reverse transcriptase activity with the RNA template at approximately 1.4 mM manganese. Substituting the bicine buffer both increased and broadened the optimal $Mn^{+2}$ concentration for each reaction. Using the bicine buffer, maximum synthesis with DNA templates was shifted to 1.5 mM manganese, while increases in the amount synthesized with RNA templates were seen up to 6 mM manganese. Although the $Mn^{+2}$ optima for rTth DNA polymerase reverse transcriptase activity on RNA templates and DNA polymerase activity on DNA templates are still different for the individual reactions when using a bicine buffer, a single $Mn^{+2}$ concentration of about 3.2 mM for a homogeneous RT/PCR appears to be at least as efficient as the RT/PCR conditions using a Tris buffer described in Example 10, above. However, the range of usable manganese concentrations for each reaction has been greatly expanded. This is a surprising result because expansion of the dual range would not have been predicted given the general theory and literature behind metal buffers.

Example XV

RT/PCR using HIV templates, Tricine and Bicine Buffers

A titration series of MnCl₂ concentration was used in RT/PCRs using HIV templates in both tricine and bicine buffers. Reactions were carried out in a 100 μl total reaction volume essentially as described in Example XVII, below. Specific reaction conditions were as follows:

200 copies HIV cRNA (pNAS-2)
1 μg poly rA
13% glycerol (w/v)
150 μM each dATP, dCTP, dGTP, dTTP
200 μM dUTP
0.20 μM each SK431 (SEQ ID No. 6), SK462 (SEQ ID No. 5)
2 units UNG*
10 units rTth* DNA polymerase
65 mM KCl
50 mM Tricine-KOH (pH 8.3) or Bicine-KOH (pH 8.3)
MnCl₂ (1.0, 1.2, 1.5, 1.75, 2.0, 2.5 mM)

*Developed and manufactured by Hoffmann-La Roche Inc. and commercially available from Perkin Elmer, Norwalk, Conn.

Reaction buffers contained 150 μM dTTP in addition to 200 μM dUTP because of the high percentage of adenine in the HIV RNA target and the reduced efficiency with which the Tth DNA polymerase incorporates dUMP during reverse transcription. The thermocycling profile was essentially as described in Example XVII, except that the reverse transcription step was carried out at 70° C. for 15 minutes. Amplified product was analyzed by gel electrophoresis as described in Example XVII.

The target was found to be reverse transcribed and amplified in both the bicine and tricine buffers within a $Mn^{+2}$ concentration range of from 1.0 to 2.5 mM, with higher levels of product formation found within a $Mn^{+2}$ concentration range of from 1.2 to 2.0 mM.

Example XVI

Increased dNTP Tolerance

To assess the increase in dNTP concentration tolerance using a bicine/KOAc/Mn(OAc)₂ buffer, RT/PCR amplifications of HCV cRNA target (pHCV 1.1 A) was carried out using both bicine and Tris buffers at varying dNTP concentrations. Reactions were carried out essentially as described in Example XVII, below, except for modifications described herein.

HCV cRNA target is described in Example XIII, above. Reactions were carried out in a 100 μl volume under the following conditions:

300 copies HCV cRNA
0.15 μM each KY78 (SEQ ID No. 16), KY90 (SEQ ID No. 17)
1 μg poly rA
8% glycerol
10 U rTth* DNA polymerase
2 U UNG*
dATP, dCTP, dGTP, and dUTP (100 μM each to 500 μM each)
50 mM Bicine-KOH (pH 8.3) or 10 mM Tris-HCl (pH 8.3)
100 mM KOAc (pH 7.5) or 90 mM KCl
2.5 mM Mn(OAc)₂ or 0.9 mM MnCl₂

*Developed and manufactured by Hoffmann-La Roche Inc. and commercially available from Perkin Elmer, Norwalk, Conn.

Figure 7:
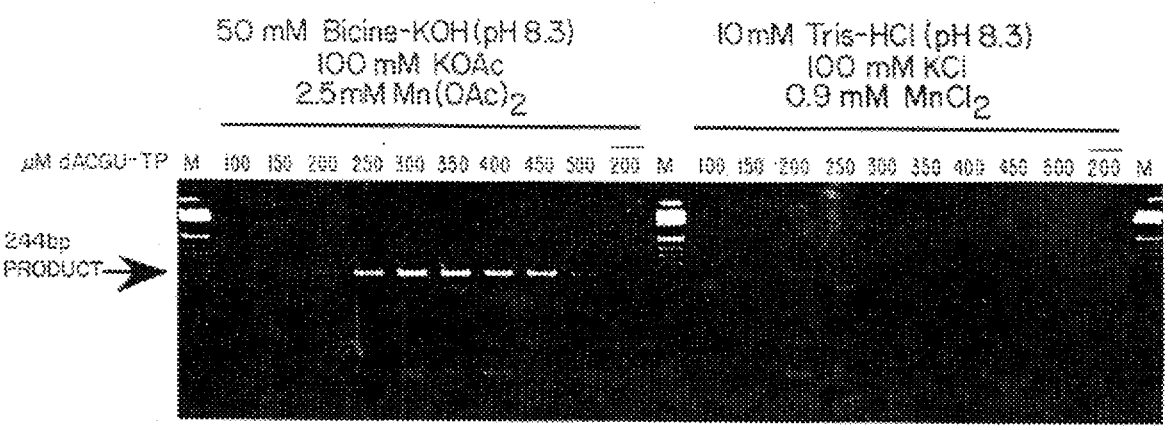
FIG. 7 depicts the results of the RT/PCR described in Example XVI, wherein the usable range of dNTP concentration is assayed using different buffer conditions.

Thermocycling parameters were essentially as described in Example XVII, below, except that the reverse transcription was at 70° C. for 25 minutes and 40 amplification cycles were performed. Amplification product was analyzed by gel electrophoresis as described in Example XVII. The results are shown in FIG. 7.

The formation of amplification product using the bicine/KOAc/Mn(OAc)₂ buffer was observed over a range of dNTP concentration from 100 to 500 μM each dNTP. In contrast, significant levels of amplification product were formed using the Tris/KCl/MnCl₂ buffer only at a 200 μM each dNTP concentration.

Example XVII

Homogeneous RT/PCR using HCV and HIV Templates

RT/PCR amplification based assays for the detection of hepatitis C virus (HCV) are described in copending U.S. Ser.

No. 07/918,884, filed Jul. 21, 1992, and in Young et al., 1993, supra, each incorporated herein by reference. The '844 application describes detection of the amplified product using a microwell plate detection format. Similar assays are useful for the detection of human immunodeficiency virus (HIV). The homogeneous RT/PCR methods of the present invention are useful for the amplification of HIV and HCV viral templates using the protocols described below. Homogeneous reactions using both bicine/KOAc/Mn(OAc)$_2$ and Tris/KCl/MnCl$_2$ buffers are described below; the use of the bicine/KOAc/Mn(OAc)$_2$ buffer is preferred. Sample template may be either from clinical samples or the HIV and HCV templates described in Example XIII, above. Suitable method for the preparation of clinical sample preparation are described in the above cited HCV assay references.

Preferred primers for the RT/PCR amplification of HIV templates are the 5' biotinylated derivatives of SK431 (SEQ ID No. 6) and SK462 (SEQ ID No. 5). Preferred primers for the RT/PCR amplification of HCV templates are KY78 (SEQ ID No. 16) and KY90 (SEQ ID No. 17).

Reaction conditions for HIV and HCV RT/PCR using Bicine-KOH (pH 8.3), KOAc (pH 7.5), and Mn(OAc)$_2$ in 100 μl total reaction volume are provided below. The HIV reaction conditions illustrate the use of an increased dUTP concentration to facilitate the incorporation of dUMP.

| For HIV templates: | For HCV templates: |
|---|---|
| 15% glycerol (w/v) | 10% glycerol (w/v) |
| 300 μM dATP | 200 μM dATP |
| 300 μM dCTP | 200 μM dCTP |
| 300 μM dGTP | 200 μM dGTP |
| 50 μM dTTP | |
| 500 μM dUTP | 200 μM dUTP |
| 20 pmol/rxn upstream primer | 15 pmol/rxn upstream primer |
| 20 pmol/rxn downstream primer | 15 pmol/rxn downstream primer |
| 2 units UNG* | 2 units UNG* |
| 10 units rTth* DNA polymerase | 15 units rTth* DNA polymerase |
| 50 mM Bicine-KOH pH 8.3 | 50 mM Bicine-KOH pH 8.3 |
| 100 mM KOAc pH 7.5 | 100 mM KOAc pH 7.5 |
| 3.6 mM Mn(OAc)$_2$ | 3.5 mM Mn(OAc)$_2$ |

*Developed and manufactured by Hoffmann-La Roche Inc. and commercially available from Perkin Elmer, Norwalk, CT.

Reaction conditions for Tris-HCl (pH 8.3), KCl, MnCl$_2$ in 100 μl total reaction volume:

| For HIV templates: | For HCV templates: |
|---|---|
| 15% glycerol (w/v) | 10% glycerol (w/v) |
| 150 μM dATP | 200 μM dATP |
| 150 μM dCTP | 200 μM dCTP |
| 150 μM dGTP | 200 μM dGTP |
| 150 μM dTTP | |
| 200 μM dUTP | 200 μM dUTP |
| 20 pmol/rxn upstream primer | 15 pmol/rxn upstream primer |
| 20 pmol/rxn downstream primer | 15 pmol/rxn downstream primer |
| 2 units UNG* | 2 units UNG* |
| 10 units rTth* polymerase | 10 units rTth* polymerase |
| 90 mM KCl | 90 mM KCl |
| 10 mM Tris-HCl pH 8.3 | 10 mM Tris-HCl pH 8.3 |
| 0.85 mM MnCl$_2$ | 0.90 mM MnCl$_2$ |

*Developed and manufactured by Hoffmann-La Roche Inc. and commercially available from Perkin Elmer, Norwalk, CT.

Reactions are carried out in a TC9600 thermal cycler (Perkin Elmer, Norwalk, Conn.). The thermal cycler is programmed to provide the following temperature profile for the amplification of HIV template:

50° C. for 2 minutes for the UNG sterilization;

60° C. for 30 minutes for the reverse transcription step;

4 cycles of (95° C. for 10 seconds, 55° C. for 10 seconds, 72° C. for 10 seconds);

24 cycles (Microwell Plate assay) or 36 cycles (Agarose Gel Analysis) of (90° C. for 10 seconds, 60° C. for 10 seconds, 72° C. for 10 seconds); and hold at 72° C.

The thermal cycler is programmed to provide the following temperature profile for the amplification of HCV template:

50° C. for 2 minutes for the UNG sterilization;

60° C. for 30 minutes for the reverse transcription;

2 cycles of 95° C. for 15 seconds, 60° C. for 20 seconds;

38 cycles of 90° C. for 15 seconds, 60° C. for 20 seconds;

60° C. for 4 minutes; and hold at 72° C.

Amplification product is analyzed either by visualization following agarose gel electrophoresis or by a microwell plate assay. For agarose gel analysis, 5 μl of each reaction are added to 2 μl of load buffer (30% sucrose, 0.1% Bromophenol blue, 10 mM EDTA) and analyzed by 4% (3% NuSieve, 1% Agarose) agarose gel electrophoresis in 1× Tris-borate EDTA with ethidium bromide (10 μg per 100 ml of agarose) added into the agarose. Electrophoresis is at 125 V for 30 minutes.

Microwell plate analysis for HCV is described in copending Ser. No. 07/918,844, filed Jul. 21, 1992, and, in general, in copending Ser. No. 414,542, filed Sep. 29, 1989, and copending Ser. No. 695,072, filed May 3, 1991, each incorporated herein by reference. Microwell plate analysis of HIV amplification product is as described for HCV but using the HIV specific probes described in Jackson et al, 1991, AIDS 5:1463–1467, incorporated herein by reference.

Example XVIII

RNA Stability

To assay the stability of RNA using different buffer conditions, RNA was incubated at elevated temperatures in reaction mixtures similar to those of a reverse transcription reaction but with the polymerase omitted to insure that no synthesis occurred. The reaction mixtures (20 μl volume each) consisted of the following:

100 ng [$^{33}$p] labeled pAW109 cRNA 1.5 μM KY80 (SEQ ID No. 17)

200 μM each dATP, dCTP, dGTP, and dUTP

2 μl rTth. DNA polymerase storage buffer (equivalent to 5 units of polymerase)

Buffer conditions were varied by the addition to the above reagents of the buffer reagents described below. All reaction mixtures were incubated at 70° C. for 25 minutes with the exception of sample 1 which was incubate at 4° C. for 25 minutes for comparison. The amount of full length RNA recovered was determined using an Ambis 4000 Radioanalytic Imaging System (Ambis, Inc., San Diego, Calif.) following gel electrophoresis. All values were normalized using the results of sample 2 as 100%. Bicine-KOH and Tris-HCl were added at pH 8.3; KOAc at pH 7.5.

| Added Reagents | Amount Recovered |
|---|---|
| 1. None added (4° C. incubation) | 113% |
| 2. None added (70° C. incubation) | 100% |
| 3. 2.5 mM Mn(OAc)$_2$ | 6% |

| Added Reagents | Amount Recovered |
|---|---|
| 4. 2.5 mM Mn(OAc)₂; 100 mM KOAc | 1% |
| 5. 2.5 mM Mn(OAc)₂; 50 mM Bicine-KOH | 3% |
| 6. 2.5 mM Mn(OAc)₂; 100 mM KOAc; 50 mM Bicine-KOH | 25% |
| 7. *2.0 mM Mn(OAc)₂; 100 mM KOAc; 50 mM Bicine KOH | 47% |
| 8. 2.5 mM Mn(OAc)₂; 100 mM KOAc; 50 mM Bicine KOH | 29% |
| 9. 3.0 mM Mn(OAc)₂; 100 mM KOAc; 50 mM Bicine KOH | 25% |
| 10. 0.9 mM MnCl₂ | 40% |
| 11. 1.0 mM MnCl₂ | 36% |
| 12. 1.0 mM MnCl₂; 90 mM KCl; 10 mM Tris-HCl | 16% |

*Sample 7 had an additional 100 µM of each dNTP (300 µM each dNTP).

The addition of manganese, which catalyzes the hydrolysis of RNA, increases the degradation of RNA at high temperatures as can be seen comparing samples 2 and 3. The addition of a buffer containing 2.5 mM Mn(OAc)₂, 100 mM KOAc, and 50 mM Bicine-KOH significantly reduced RNA degradation. Comparing samples 3, 4, 5, and 6 indicates that all components of the buffer must be present to decrease the amount of RNA degradation observed. The Mn(OAc)₂/KOAc/Bicine-KOH buffers decreased the amount of RNA degradation relative to the MnCl₂/KCl/Tris-HCl buffers as can be seen comparing samples 6–9 to sample 12.

A high temperature preincubation will facilitate the amplification of double-stranded RNA targets as well as targets with a high degree of secondary structure by denaturing the RNA prior to reverse transcription. To assess the effect of a high temperature preincubation on the stability of RNA in a bicine/KOAc/Mn(OAc)₂ buffer, RNA was incubated at elevated temperatures in reaction mixtures similar to those of a reverse transcription reaction but with the polymerase omitted to insure that no synthesis occurred. The reaction mixtures (20 µl volume each) consisted of the following:

250 ng [³³p] labeled pAW109 cRNA
1.5 µM DM151 (SEQ ID No. 10)
300 µM each dATP, dCTP, dGTP, and dUTP
50 mM Bicine-KOH (pH 8.3)
100 mM KOAc (pH 7.5)
2.5 mM Mn(OAc)₂
2 µl rTth DNA polymerase storage buffer (equivalent to 5 units of polymerase)

The reaction mixtures were incubated at the temperatures shown below and the final amount of full length RNA was determined using an Ambis 4000 Radioanalytic Imaging System (Ambis Inc., San Diego, Calif.) following gel electrophoresis. Incubations were done in triplicate and the average amount of undegraded RNA remaining was normalized to the amount remaining after a 25 minute 4° C. incubation. The average standard deviation for the amount recovered from the 3 reaction incubations within a group was 11%.

| Incubation Temperature | Amount Recovered |
|---|---|
| 4° C. for 25 minutes | 100% |
| 95° C. for 15 seconds, 4° C. for 25 minutes | 84% |
| 60° C. for 25 minutes | 66% |
| 95° C. for 15 seconds, 60° C. for 25 minutes | 68% |

An incubation of 60° C. for 25 minutes is comparable to the conditions of a reverse transcription as described in the previous examples. No detectable additional loss of full length labeled RNA occurred when a 15 second, 95° C. preincubation of the RNA was included.

Example XIX

Effect of Manganese Concentration on RT/PCR using HCV Templates

RT/PCR amplification reactions were carried out over a range of manganese concentrations using both bicine/KOAc/Mn(OAc)₂ and Tris/KCl/MnCl₂ buffers. Reaction conditions for the HCV RT/PCR in 100 µl total reaction volume are provided below.

100 copies HCV cRNA
200 µM dATP
200 µM dCTP
200 µM dGTP
200 µM dUTP
15 pmol/rxn KY78 (SEQ ID No. 16)
15 pmol/rxn KY90 (SEQ ID No. 17)
2 units UNG*
10 units rTth* DNA polymerase
8% glycerol (w/v)

| | | |
|---|---|---|
| 50 mM Bicine-KOH (pH 8.3) | or | 10 mM Tris-HCl (pH 8.3) |
| 100 mM KOAc (pH 7.5) | or | 90 mM KCl |
| Mn(OAc)₂ | or | MnCl₂ |

*Developed and manufactured by Hoffmann-La Roche Inc. and commercially available from Perkin Elmer, Norwalk, CT.

The manganese concentrations used were 1.5, 2.0, 2.5, 3.0, 3.5, and 4.0 mM Mn(OAc)₂ and 0.7, 0.8, 0.85, 0.9, 0.95, and 1.0 mM MnCl₂. Reactions were carried out in a TC9600 thermal cycler (Perkin Elmer, Norwalk, Conn.). The thermal cycler was programmed to provide the temperature profile described in Example XVII, with the exception that the reverse transcription was performed at 70° C. for 25 minutes followed by a 1 minute incubation at 95° C. Amplification product was analyzed by visualization following agarose gel electrophoresis as described in Example XVII.

Amplification product was observed using the bicine/KOAc/Mn(OAc)₂ buffer for a Mn(OAc)₂ concentration range of 2.0–4.0 mM. Amplification product was observed using the Tris/KCl/MnCl₂ buffer for a MnCl₂ concentration range of 0.8–1.0 mM. Under these reaction conditions, product was observed over a 10-fold greater range of manganese concentration using the bicine/KOAc/Mn(OAc)₂ buffer as compared to the Tris/KCl/MnCl₂ buffer.

Example XX

RT/PCR Using a High Tris Concentration

RT/PCR amplification reactions were carried out over a range of manganese concentrations using Tris/KCl/MnCl₂ buffers with two concentrations of Tris. Reaction conditions for the HCV RT/PCR in 100 µl total reaction volume are provided below.

500 copies HCV cRNA
200 µM dATP
200 µM dCTP
200 µM dGTP
200 µM dUTP
15 pmol/rxn KY78 (SEQ ID No. 16)
15 pmol/rxn KY80 (SEQ ID No. 17)
2 units UNG*
10 units rTth* DNA polymerase
8% glycerol (w/v)

10 mM Tris-HCl (pH 8.3) or 100 mM Tris-HCl (pH 8.3)
90 mM KCl or 45 mM KCl
$MnCl_2$

*Developed and manufactured by Hoffmann-La Roche Inc. and commercially available from Perkin Elmer, Norwalk, Conn.

The manganese concentrations used were 0.7, 0.8, 1.0, 1.2 and 1.3 mM $MnCl_2$ for each Tris concentration. Reactions were carried out in a TC9600 thermal cycler (Perkin Elmer, Norwalk, Conn.). The thermal cycler was programmed to provide the temperature profile described in Example XVII, with the exception that the reverse transcription was performed at 70° C. for 25 minutes followed by a 1 minute incubation at 95° C. Amplification product was analyzed by visualization following agarose gel electrophoresis as described in Example XVII.

Amplification product was observed using the 100 mM Tris buffer for a $MnCl_2$ concentration range of 0.7–1.2 mM. Amplification product was observed using the 10 mM Tris buffer for a $MnCl_2$ concentration range of 0.8–1.0 mM. Under these reaction conditions, product was observed over a greater range of manganese concentration when the concentration of Tris in a Tris/KCl/$MnCl_2$ buffer was increased from 10 to 100 mM.

Deposition of Cultures

The cultures were deposited in the American Type Culture Collection (ATCC), 12301 Parklawn Drive, Rockville, Md., USA. The ATCC accession numbers and ATCC deposit dates for the deposited samples are given below:

| Culture | ATCC No. | Deposit Date |
| --- | --- | --- |
| pBSM:Tth10 | 68195 | 12/21/89 |
| pAW109 | 68152 | 10/27/89 |

These deposits were made under the Budapest Treaty on the International Recognition of the Deposit of Microorganisms for the Purpose of (Budapest Treaty). This assures maintenance of a viable culture for 30 years from date of deposit. The deposits will be made available by ATCC under the terms of the Budapest treaty, and subject to an agreement between applicants and ATCC which assures permanent and unrestricted availability upon issuance of the pertinent U.S. patent. The Assignee herein agrees that if the culture on deposit should die or be lost or destroyed when cultivated under suitable conditions, it will be promptly replaced upon notification with a viable specimen of the same culture. Availability of the deposits is not to be construed as a license to practice the invention in contravention of the rights granted under the authority of any government in accordance with its patent laws.

These deposits were made for the convenience of the relevant public and do not constitute an admission that a written description would not be sufficient to permit practice of the invention or an intention to limit the invention to these specific constructs. Set forth hereinabove is a complete written description enabling a practitioner of ordinary skill to duplicate the constructs deposited and to construct alternative forms of DNA, or organisms containing it, which permit practice of the invention as claimed.

The invention has been described in detail, but it will be understood that variations and modifications can be effected within the spirit and scope of the following claims.

We claim:

1. A homogeneous reverse transcription/amplification reaction mixture comprising an RNA template, a purified thermostable DNA polymerase, a primer, four different nucleoside triphosphates, a divalent cation, a monovalent cation, and a buffering agent, wherein the divalent cation is $Mn^{+2}$ and the buffering agent is N,N-Bis(hydroxyethyl)glycine or Tris(hydroxymethyl)methylglycine.

2. The reaction mixture of claim 1, wherein said divalent cation is supplied by manganese acetate, manganese chloride, or manganese sulfate, and said monovalent cation is supplied by a salt selected from the group consisting of sodium acetate, potassium acetate, ammonium acetate, lithium acetate, sodium chloride, potassium chloride, ammonium chloride, and lithium chloride.

3. The reaction mixture of claim 2, wherein said buffering agent is N,N-Bis(hydroxyethyl)glycine.

4. The reaction mixture of claim 3, wherein said buffering agent is Tris(hydroxymethyl)methylglycine.

5. The reaction mixture of claim 2, wherein said divalent cation is supplied by manganese acetate at a concentration of between 1.2 and 5 mM.

6. The reaction mixture of claim 5, wherein said monovalent cation is supplied by potassium acetate.

* * * * *